United States Patent [19]

Halazy et al.

[11] Patent Number: 5,789,412
[45] Date of Patent: Aug. 4, 1998

[54] PIPERAZIDES DERIVED FROM ARYLPIPERAZINE, PROCESSES FOR THEIR PREPARATION, THEIR USE AS MEDICAMENTS AND PHARMACEUTICAL COMPOSITIONS COMPRISING THEM

[75] Inventors: Serge Halazy, Lagarrigue; Catherine Jorand, Castres; Peter Pauwels, Lautrec, all of France

[73] Assignee: Pierre Fabre Medicament, Boulogne, France

[21] Appl. No.: 776,057

[22] PCT Filed: Jul. 20, 1995

[86] PCT No.: PCT/FR95/00975

§ 371 Date: Jan. 20, 1997

§ 102(e) Date: Jan. 20, 1997

[87] PCT Pub. No.: WO96/02525

PCT Pub. Date: Feb. 1, 1996

[30] Foreign Application Priority Data

Jul. 20, 1994 [FR] France ................... 94 08981

[51] Int. Cl.$^6$ ............... A61K 31/495; C07D 401/14; C07D 403/12
[52] U.S. Cl. ........................... 514/255; 544/357
[58] Field of Search ................. 544/357; 514/255

[56] References Cited

FOREIGN PATENT DOCUMENTS

| 533266 | 3/1993 | European Pat. Off. . |
| 533267 | 3/1993 | European Pat. Off. . |
| 533268 | 3/1993 | European Pat. Off. . |
| 2699918 | 7/1994 | France . |
| 2097790 | 11/1982 | United Kingdom . |

OTHER PUBLICATIONS

Popescu, *Chemical Abstracts*, vol. 68, No. 105151, 1968.
Pestellini et al, *Chemical Abstracts*, vol. 90 No. 132586, 1979.
Millan et al, Journal of Pharmacology and Experimental Therapeutics, 262, pp. 451–463, 1992.
Buzzi et al, *Chephalagia* 15, pp. 277–280, 1995.

*Primary Examiner*—Emily Bernhardt
*Attorney, Agent, or Firm*—The Firm of Gordon W. Hueschen

[57] ABSTRACT

Novel 5HT receptor antagonists of general formula (I)

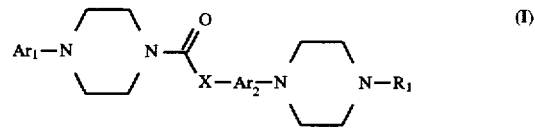

in which $Ar_1$ and $Ar_2$ are aromatic residues, X is O, NH, $CH_2O$, or $CH_2NH$, and $R_1$ is hydrogen or linear or branched alkyl comprising 1–6 carbon atoms, as well as their salts, hydrates, solvates, and physiologically-acceptable bioprecursors for their therapeutic use, their geometric and optical isomers, and their mixtures in all proportions and in racemic form, methods for the preparation of these novel antagonists, and their use in the treatment of a living animal and pharmaceutical compositions comprising them.

38 Claims, No Drawings

PIPERAZIDES DERIVED FROM ARYLPIPERAZINE, PROCESSES FOR THEIR PREPARATION, THEIR USE AS MEDICAMENTS AND PHARMACEUTICAL COMPOSITIONS COMPRISING THEM

The present application is a U.S. National Application filed under 35 USC 371 of PCT/FR95/00975, filed Jul. 20, 1995 based upon a French application Ser. No. 94/08981 filed Jul. 20, 1994.

The present invention relates to novel piperazides derived from arylpiperazine, as well as to a process for their preparation, to pharmaceutical compositions containing them and to their use as medicaments.

Serotonin or 5-hydroxytryptamine (5-HT) is a neurotransmitter and a neuromodulator of the central nervous system involved in many physiological and pathological processes. Serotonin plays an important role not only in the nervous system but also in the cardiovascular and gastrointestinal systems. At the central level, serotonin controls functions as varied as sleep, locomotion, feeding, learning and memory, endocrine modulations, sexual behavior and temperature regulation. In the spinal column, serotonin plays an important role in the control systems of the afferent peripheral nociceptors (cf. A. Moulignier, Rev. Neurol. (Paris), 150, 3–15, 1994).

Serotonin may play an important role in various types of pathological conditions such as certain psychiatric disorders (anxiety, depression, aggressiveness, panic attacks, obsessive compulsive disorders, schizophrenia, suicidal tendency), certain neurodegenerative disorders (Alzheimer-type dementia, Parkinsonism, Huntington'chorea), anorexia, bulimia, disorders associated with alcoholism, cerebral vascular accidents, migraine or various headaches (R. Glennon, Neurosci. Biobehavioral Reviews, 14, 35, 1990).

Many recent pharmacological studies have demonstrated the diversity of the serotonin receptors and their respective involvement in these various modes of action (cf. E. Zifa, G. Fillion, Pharm Reviews, 44, 401, 1992; S. Langer, N. Brunello, G. Racagni, J. Mendlecvicz, "Serotonin receptor subtypes: pharmacological significance and clinical implications", Karger Ed. (1992); B. E. Leonard, Int. Clin. Psycho-pharmacology, 7, 13–21 (1992); R. W. Fuller, J. Clin. Psychiatry, 53, 36–45 (1992); D. G. Grahame-Smith, Int. Clin. Psychopharmacology, 6, suppl. 4, 6–13, (1992). These receptors are mainly subdivided into 4 major classes ($5HT_1$, $5HT_2$, $5HT_3$ and $5HT_4$) which themselves contain subclasses, such as the $5HT_1$ receptors which are mainly divided into $5HT_{1A}$, $5HT_{1B}$ and $5HT_{1D}$ (cf. G. R. Martin, P. A. Humphrey, Neuropharmacol., 33, 261, 1994; P. R. Saxena, Exp. Opin. Invest. Drugs, 3 (5), 513, 1994). The $5HT_{1D}$ receptors themselves contain several receptor subtypes; thus, the $5HT_{1D\alpha}$ and $5HT_{1Db}$ receptors have been cloned and then identified in man (cf. for example E. Hamel et al., Mol. Pharmacol., 44, 242, 1993; G. W. Rebeck et al., Proc. Natl. Acad. Sci. USA, 91, 3666, 1994). Moreover, it has recently been demonstrated that the $5HT_{1B}$ self-receptors in rodents and $5HT_{1D}$ in other species were capable of controlling the release of serotonin in nerve endings (cf. M. Briley, C. Moret, Cl. Neuropharm. 16, 387, 1993; B. E. Leonard, Int. Clin. Psychopharmacol., 9, 7, 1994) as well as the release of other neurotransmitters such as norepinephrine, dopamine or acetylcholine (M. Harrigton, J. Clin. Psychiatry, 53, 10, 1992).

Compounds having a selective antagonist activity towards the central $5HT_{1D}$ receptors, such as the novel compounds described in the present invention, can thus exert a beneficial effect on individuals suffering from central nervous system disorders. In particular, such compounds are useful in the treatment of pain, cancer, locomotion disorders, depression, anxiety, panic attacks, agoraphobia, obsessive compulsive disorders, memory disorders including dementia, amnesia, appetite disorders, sexual dysfunctioning, Alzheimer's disease and Parkinson's disease. $5HT_{1D}$ antagonists are also useful in the treatment of endocrine disorders such as hyperprolactinaemia, the treatment of vasospasms, of hypertension and of gastrointestinal disorders in which changes in motility and in secretion are involved.

The compounds according to the present invention are powerful and selective antagonists of $5HT_{1D}$ receptors and more particularly of the receptors recently identified as $5HT_{1D\alpha}$ and $5HT_{1D\beta}$ in man and are consequently useful, alone or in combination with other molecules, as medicaments and more particularly as therapeutic means for both the curative and preventive treatment of disorders associated with serotonin.

The prior art in this field is illustrated in particular by European patent applications 0.533.266, 0.533.267 and 0.533.268 which describe novel benzanilide derivatives as $5HT_{1D}$ antagonists and recent publications which describe GR 127.935 as a $5HT_{1D}$ antagonist (cf. M. Skingle et al., J. of Psychopharm. 8 (1), 14, 1994; S. Starkey, M. Skingle, Neuropharmacol., 33, 393, 1994).

The derivatives of the present invention are distinguished from the prior art not only by their original chemical structure which distinguishes them unambiguously from the derivatives described previously but also by the efficacy of their preparation (overall yield, number of steps) and their original biological profile, in particular as regards their selectivity for serotonin receptor subtypes ($5HT_{1D}\alpha$ and $\beta$)

The present invention relates to derivatives of general formula (I)

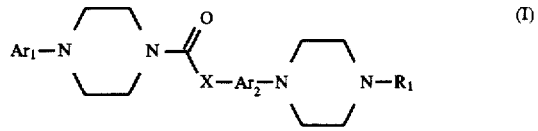

in which

Ar₁ represents an aromatic residue such as a phenyl, a naphthyl or a pyridyl, or an aromatic residue substituted with one or more groups chosen from linear or branched alkyl residues comprising from 1 to 6 carbon atoms, trifluoromethyl, 2,2,2-trifluoroethyl, phenyl, benzyl, cycloalkyl, hydroxyl (OH), thiol (SH), ether (OR'₂), thioether (SR'₂), ester (OCOR'₂), carbamate (OCONHR₂), carbonate (OCO₂R'₂), carbonyls (COR₂, COOR'₂, CONHR₂), halogens (fluorine, chlorine, bromine or iodine), amine (NR₂R₃), nitro (NO₂), nitrile (CN), aminocarbonyl (NHCOR'₂, NHCO₂R'₂, NHCONR₂R₃), aminosulfonyls (NHSO₂R'₂, N(SO₂R'₂)₂, NHSO₂OR'₂, NHSO₂NR₂R₃), sulfonyls (SO₂R'₂, SO₂NR₂R₃) and heterocycles which can optionally be variously substituted, such as a 5-membered heterocycle which may contain from 1 to 4 hetero atoms such as oxygen, nitrogen or sulfur, or two substituents on neighboring carbons which can form a ring with the aromatic residue to which they are attached, X represents O, NH, CH₂O or CH₂NH, Ar₂ represents an aromatic radical such as a phenyl or a naphthyl to which X and the piperazine are attached on different carbons and which can itself be variously substituted by a linear or branched alkyl radical comprising from 1 to 6 carbon atoms, an alkoxy (OR$_4$) or a halogen (chlorine, fluorine, iodine or bromine), R$_1$, R$_2$, R$_3$ and R$_4$, which are identical or different, represent a hydrogen or a linear or branched alkyl chain comprising from 1 to 6 carbon atoms, R'$_2$ represents a linear or branched alkyl chain comprising from 1 to 6 carbon atoms, and their salts, hydrates, solvates and bioprecursors which are physiologically acceptable for their therapeutic use.

The geometrical and optical isomers of the compounds of general formula (I) also form part of the present invention, along with mixtures thereof in all proportions and in racemic form.

Among the physiologically acceptable salts of the compounds of general formula (I) are included the salts obtained by addition of organic or inorganic acids such as the hydrochlorides, hydrobromides, sulfates, phosphates, benzoates, acetates, naphthoates, p-toluenesulfonates, methanesulfonates, sulfamates, ascorbates, tartrates, citrates, oxalates, maleates, salicylates, fumarates, succinates, lactates, glutarates and glutaconates.

The expression "bioprecursors" as used in the present invention applies to compounds whose structure differs from that of the compounds of formula (I) but which, when administered to an animal or to a human being, are converted in the body into a compound of formula (I).

A particularly valuable class of compounds of formula (I) corresponds to the compounds for which Ar$_2$ represents a phenyl which may be variously substituted, in particular the compounds of formula (Ia):

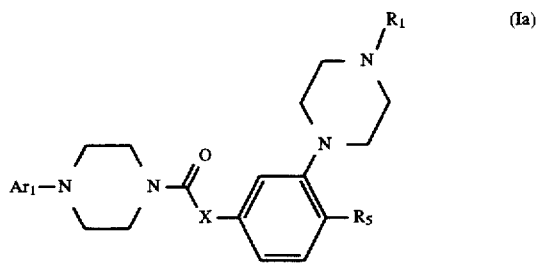

in which Ar$_1$, X and R$_1$ are defined as in formula (I) and R$_5$ represents a hydrogen atom, a linear or branched alkyl radical comprising from 1 to 6 carbon atoms, an alkoxy (OR$_4$) or a halogen (chlorine, fluorine, iodine or bromine), R$_4$ being defined above.

Another particularly valuable class of compounds of formula (I) corresponds to the compounds for which Ar$_2$ represents a naphthyl, in particular the compounds of formula (Ib):

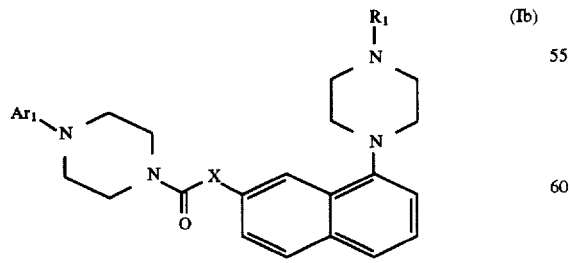

in which Ar$_1$, X and R$_1$ are defined as in general formula (I).

When Ar$_1$ represents an aryl in which two substituents on neighboring carbons form a ring with the aromatic residue, this is advantageously a phenyl in which two substituents on neighboring carbons form with the phenyl to which they are attached a 5- or 6-membered ring which can comprise 1 or 2 hetero atoms (oxygen, nitrogen or sulfur).

The compounds of the present invention may be prepared by various methods which will be dependent in particular on the nature of the substituents Ar$_1$, Ar$_2$, X and R$_1$.

It will be understood that in certain chemical reactions or reaction sequences which lead to the preparation of compounds of general formula (I) it is necessary or desirable to protect possible sensitive groups in the synthesis intermediates in order to prevent undesirable side reactions. This may be carried out by the use (introduction and deprotection) of conventional protecting groups such as those described in "Protective groups in Organic Synthesis", T. W. Greene, John Wiley & Sons, 1981 and "Protecting Groups", P. J. Kocienski, Thieme Verlag, 1994. The appropriate protecting groups will thus be introduced and removed during the step which is most suitable to do this and using the methods and techniques described in the references cited above.

The compounds of general formula (I) in which Ar$_1$, Ar$_2$ and R$_1$ are described as above and X represents —CH$_2$O— or —CH$_2$NH— are prepared by condensation of an intermediate of general formula (II):

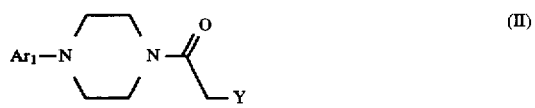

in which Ar$_1$ is defined as above and Y represents a leaving group such as a halogen (chlorine, bromine or iodine) a toxylate [sic], a mesylate or a triflate with an arylpiperazine of general formula (III):

in which X' represents O or NH, Ar$_2$ represents an aromatic ring such as a phenyl or naphthyl onto which X' and the piperazine ring are attached at different positions and R$_1$ is described as above. The condensation of the arylpiperazines of formula (III) with electrophiles of formula (II) is carried out in the presence of an organic or inorganic base such as NaH, KH, DiPEA, DBU, pyridine, DMAP, K$_2$CO$_3$, CaCO$_3$, Cs$_2$CO$_3$, optionally in the presence of an iodide such as NaI, KI, Bu$_4$NI in a polar anhydrous solvent such as THF, DME, n-butanol, t-butanol, DMF, DMSO or methyl ethyl ketone, at a temperature of between 20° and 80°. The intermediates of general formula (II) are readily prepared by condensation of an arylpiperazine of general formula (IV)

in which Ar$_1$ is defined as above, with an acid chloride of general formula (V):

in which Y is described as above, in the presence of an organic or inorganic base such as pyridine, DiPEA, DMAP, DBU, K$_2$CO$_3$, Cs$_2$CO$_3$ or CaCO$_3$ in a polar aprotic anhydrous solvent such as THF, DMF, DME, DMSO or methyl ethyl ketone at a temperature of between −10° C. and 80° C.

The intermediates of general formulae (III) and (IV) are prepared by various methods and techniques which are well known to those skilled in the art for the preparation of arylpiperazines and whose choice is dependent on the nature of X', of $Ar_2$, of $Ar_1$ and of $R_1$. Thus, in the specific case in which X' is an oxygen, the intermediates of formula (III) are accessible by condensation of an arylamine of formula (VI):

(VI)

in which $Ar_2$ is defined as above, with an amine derivative of formula (VII):

(VII)

in which $R'_1$ is equivalent to $R_1$ as described above, where $R'_1$ represents a protecting group such as t-butoxycarbonyl or a tosyl which will be converted into $R_1$ subsequently, and Y represents a chlorine, a bromine, an iodine, a tosylate or a mesylate. This reaction is preferably carried out in a polar anhydrous solvent such as DMF, acetonitrile, THF, n-butanol, t-butanol or DMSO, generally at the reflux temperature of the solvent used, in the presence of an organic or inorganic base generally used for this type of reaction, such as a potassium, sodium or calcium carbonate.

In certain specific cases, the derivatives of formula (III) in which X' is an oxygen are preferably prepared by reaction of a lithiopiperazine of formula VIII in which $R_1$ is defined as above:

(VIII)

with a symmetrical aromatic bis-methoxy of general formula (IX)

(IX)

in which $Ar_2$ represents a phenyl or a naphthyl, under the conditions described above (cf: J. Org. Chem. 58, 5101, 1993), followed by demethylation of the arylmethoxy group with a suitable reagent such as $BBr_3$ in dichloromethane.

The compounds of general formula (III) in which X' represents NH are prepared by condensation of an aromatic amine of general formula (X)

(X)

in which $Ar_2$ is defined as above and X" represents a function which can subsequently be converted into amine (such as, for example, a nitro group), either with a bis(haloethyl)amine derivative of formula (VII) under the conditions described above for this type of reaction, or with an amino acid of general formula (XI)

(XI)

in which $R_1$ is defined as above, in the presence of acetic anhydride, followed by reduction of the intermediate diketopiperazine thus formed with, for example, a borane. In both cases, the derivative of formula (III) will be obtained finally after conversion of the group represented by X" into amine. If this involves a nitro group, this conversion will be carried out according to the methods and techniques well known to those skilled in the art for converting a nitroaromatic into an aniline derivative, such as, for example, the use of Raney nickel or rhodium catalyst in the presence of hydrazine, hydrogenation on palladium-on-charcoal at atmospheric pressure or the use of $SnCl_2$ or zinc.

The compounds of general formula (I) in which $Ar_1$, $Ar_2$ and $R_1$ are described as above and X represents O or NH are prepared by condensation of an intermediate of general formula (III), in which X' represents O or NH, $Ar_2$ and $R_1$ are defined as above, and of an arylpiperazine of formula (IV) in which $Ar_1$ is defined as above, with a derivative of general formula (XII):

(XII)

in which $X_1$ and $X_2$, which are identical or different, each represent a leaving group such as a halogen (in particular chlorine), an O-alkyl group (in particular the $OCCl_3$ group), a succinimyl, phthalyl or imidazolyl group. The method of the present invention also comprises the use of well-known precursors or analogues of the reactants of general formula (XII). Thus, by way of example, the condensation of the intermediates (III) and (IV) with phosgene may advantageously be carried out using diphosgene or triphosgene according to a procedure which is well known to those skilled in the art.

The methods and techniques chosen to carry out the preparation of the compounds of formula (I) in which X represents O or NH by condensation of the derivatives of formula (III) in which X' represents O or NH and of derivatives of formula (IV) with a reactant of formula (XII), such as the choice of order of the reactants, the reaction times, the isolation and/or purification of the intermediates, the reaction temperature at various steps in the condensation, the nature of the solvent or solvents, the presence of co-reactants (such as an organic or inorganic base, for example a tertiary amine) or of catalysts and the choice of reactant (XII) (choice of $X_1$ and $X_2$) will be determined by the nature of $Ar_1$, $Ar_2$, X (O or NH) and $R_1$.

Thus, a particularly valuable method for preparing derivatives of formula (I) in which X=NH and $Ar_1$, $Ar_2$ and $R_1$ are defined as above consists in reacting an intermediate of formula (III), in which X' represents NH and $Ar_2$ and $R_1$ are defined as above, with triphosgene in the presence of a base such as triethylamine, in an anhydrous solvent such as dichloromethane, and in then adding a compound of formula (IV) in which $Ar_1$ is defined as above, in the presence of a base such as a tertiary amine.

In the case of the preparation of derivatives of general formula (I) in which $Ar_1$, $Ar_2$ and $R_1$ are defined as above and X represents an oxygen, a particularly valuable method consists in first condensing an arylpiperazine of formula (IV) with triphosgene in the presence of triethylamine, in an anhydrous solvent such as dichloromethane, and in isolating the intermediate of general formula (XIII) thus formed:

(XIII)

before condensing it with a nucleophile of general formula (III) in which X' represents an oxygen, in the presence of an organic or inorganic base such as NaH, KH or t-BuOK, in a polar aprotic solvent such as THF or DMF.

Methods which make it possible to prepare the products of formula (I), in which X represents O or NH, by condensation of an aromatic piperazine of formula (IV) with a derivative of general formula (XIV):

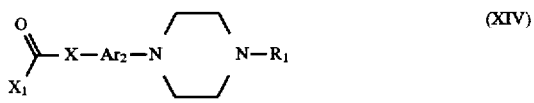

(XIV)

in which $X_1$, $Ar_2$ and R are defined as above and X represents O or NH, in the presence of an organic or inorganic base in a polar aprotic solvent at a temperature of between 20° and 100° C., should also be considered as forming part of the present invention.

In the specific case of compounds of general formula (I) in which $R_1$ represents a hydrogen, it is preferable to use, for certain reactions which require it, reaction intermediates in which $R_1$ represents a protecting group such as, for example, a t-butoxycarbonyl (BOC) which will be introduced beforehand by condensation of the appropriate intermediate in which $R_1$=H with a suitable reactant such as $(BOC)_2O$, BOC—ON=C (CN)—Ph, BOC—$ONH_2$. This will make it possible to prepare, according to the methods and techniques presented previously, intermediates of general formula (I) in which $R_1$=BOC and to convert these intermediates into final products of general formula (I) in which $R_1$=H after deprotection of the t-butylcarbonate according to methods and techniques which are well known for this type of conversion, such as the use of acid (HCl, $CF_3CO_2H$ or $H_2SO_4$) in organic medium.

Any method which makes it possible to convert a derivative of formula (I) into another derivative of formula (I) in which at least one of the substituents $Ar_1$, X, $Ar_2$ or $R_1$ are different, by methods and techniques well known to those skilled in the art should also be considered as forming an integral part of the present invention. Thus, by way of example, the derivatives of general formula (I) in which $Ar_1$ represents a phenyl substituted with an $NO_2$ group may be converted into derivatives of formula (I) in which $Ar_1$ represents a phenyl substituted in the same position with an $NH_2$ group (by methods and techniques which are well known for this type of reduction as described, for example, in "Comprehensive Organic transformation", p. 412; (R. C. Larock, VCH, 1989) among which mention may be made of atmospheric hydrogenation catalyzed by palladium-on-charcoal, the use of $SnCl_2$ or of zinc or alternatively of rhodium catalyst in the presence of hydrazine. The compounds of general formula (I) in which $Ar_1$ represents an aromatic substituted with an $NH_2$ group may themselves be converted into many other derivatives of formula (I) such as derivatives in which $Ar_1$ represents an aromatic substituted with $NR_2R_3$, $NHCOR_2$, $NHCO_2R_2$, $NHCOR_2R_3$, $NHSO_2R_2$, $NHSO_2OR_2$, $NHSO_2OR_2$, $NHSO_2NR_2R_3$ by methods and techniques which are well known for converting an aromatic amine into amide, carbonate, urea, sulfonamide, sulfonate or sulfonylurea.

When it is desired to isolate a compound according to the invention in the form of salt, for example of salt by addition with an acid, this may be achieved by treating the free base of general formula (I) with a suitable acid preferably in equivalent amount, or with creatinine sulfate in a suitable solvent.

When the processes described above for preparing the compounds of the invention give stereoisomeric mixtures, these isomers may be separated by conventional methods such as preparative chromatography.

When the novel compounds of general formula (I) possess one or more asymmetric centers, they may be prepared in the form of a racemic mixture or in the form of enantiomers either by enantioselective synthesis or by resolution. The compounds of formula (I) possessing at least one asymmetric center may, for example, be separated into their enantiomers by the usual techniques, such as the formation of diastereoisomeric pairs by formation of a salt with an optically active acid such as (−)-di-p-toluoyl-1-tartaric acid, (+)-di-p-toluoyl-1-tartaric acid, (+)-camphorsulfonic acid, (−)-camphorsulfonic acid, (+)-phenylpropionic acid or (−)-phenylpropionic acid, followed by fractional crystallization and regeneration of the free base. The compounds of formula (I) in which $R_1$ is a hydrogen comprising at least one asymmetric center can also be resolved by formation of diastereomeric amides which are separated by chromatography and hydrolyzed to remove the chiral auxiliary.

The examples which follow illustrate the invention without, however, limiting the scope thereof.

The proton NMR spectra were recorded on a Brucker AC 200 machine. The chemical shifts are expressed in ppm and the following abbreviations were used: "s" for singlet; "brs" for broad singlet, "d" for doublet, "dd" for doubled doublet, "t" for triplet, "q" for quartet, "sx" fox sextet, "m" for multiplet, "M" for unresolved complex.

The infrared spectra were recorded on a Nicolet 510P machine. The absorption bands are given in $cm^{-1}$.

The elemental analyses were performed on a Fisons EA 1108 machine.

EXAMPLE 1

N-[4-methoxy-3-(4-methylpiperazin-1-yl)phenyl]-4-(o-tolyl piperazin-1-ylamide fumarate

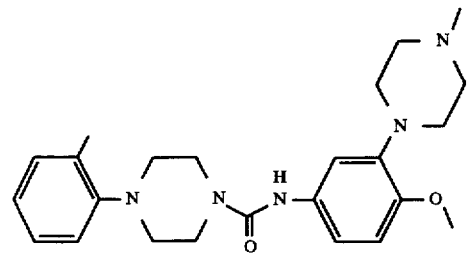

A solution of triphosgene (320 mg, 1.08 mmol) in dichloromethane (10 ml) is cannulated onto a solution of 4-methoxy-3-(4-methylpiperazin-1-yl)aniline which can be prepared according to the method described in European patent 0,533,266-A1 (714 mg, 3.23 mmol) and triethylamine (450 μl, 3.25 mmol) in dichloromethane (10 ml) under a nitrogen atmosphere. During this operation, the reaction mixture is cooled in an ice bath. It is then returned to room temperature over ½ h. After this time, N-o-tolylpiperazine (570 mg, 3.23 mmol) and triethylamine (450 μl, 3.25 mmol) diluted in dichloromethane (10 ml) are added. The reaction mixture is stirred for 12 h at room temperature and is then diluted with water and dichloromethane. The phases are separated and the organic phase dried over sodium sulfate.

The crude product obtained is purified by flash chromatography with a mixture (90/9/1) of dichloromethane/methanol/aqueous ammonia.

Mass obtained: 356 mg (yield 26%).

This compound is dissolved in methanol and treated with fumaric acid to give the corresponding fumarate. The latter is crystallized from ether.

Elemental analysis for: $C_{24}H_{33}N_5O_2 \cdot 1.5C_4H_4O_4$ Calculated. C. 60.29; H. 6.58; N. 11.72; experimental. C. 59.86; H. 6.77; N. 11.48

Mass: 424 ($MH^+$), 248, 177

IR (KBr): 3416, 2924, 1707, 1637, 1500

1H NMR (DMSO): 2.27 (s, 3H); 2.39 (s, 3H); 2.72 (m, 4H); 2.82 (m, 4H); 3.00 (m, 4H); 3.56 (m, 4H); 3.72 (s, 3H); 6.57 (s, 3H); 6.78–7.19 (m, 4H); 8.36 (s, 1H).

Melting point: 110° C.

EXAMPLE 2

N-[4-Methoxy-3-(4-methylpiperazin-1-yl)phenyl]-4-(o-methoxyphenyl)piperazin-1-ylamide fumarate

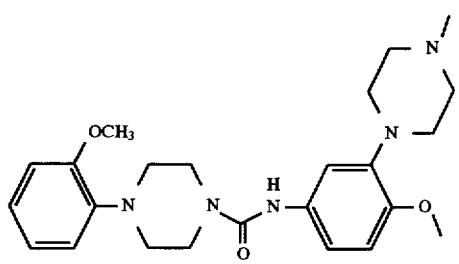

Compound 2 is prepared according to the procedure described in Example 1, using the following reactants: triphosgene (273 mg, 0.92 mmol); 4-methoxy-3-(4-methylpiperazin-1-yl)aniline (609 mg, 2.76 mmol); triethylamine (2×382 µl, 5.52 mmol); 1-(o-methoxyphenyl)piperazine (530 mg, 2.76 mmol); dichloromethane (25 ml).

The crude reaction product is purified by flash chromatography with a mixture (95/5/1) of dichloromethane/methanol/aqueous ammonia.

Mass obtained: 358 mg (yield 30%)

Elemental analysis for: $C_{24}H_{33}N_5O_3 \cdot C_4H_4O_4$ Calculated. C. 60.53; H. 6.71; N. 12.60; Experimental. C. 59.61; H. 6.90; N. 11.63

Mass: 440 ($MH^+$), 280, 248, 193

IR (KBr): 3420, 1701, 1638, 1508

1H NMR (DMSO): 2.35 (s, 3H); 2.67 (m, 4H); 3.55 (m, 4H); 3.72 (s, 3H); 3.79 (s, 3H); 6.57 (s, 2H); 6.78–7.10 (m, 7H); 8.3 (s, 1H).

Melting point: 128° C.

EXAMPLE 3

N-[4-Methoxy-3-(4-methylpiperazin-1-yl)phenyl]-4-(p-methoxyphenyl)piperazin-1-ylamide fumarate

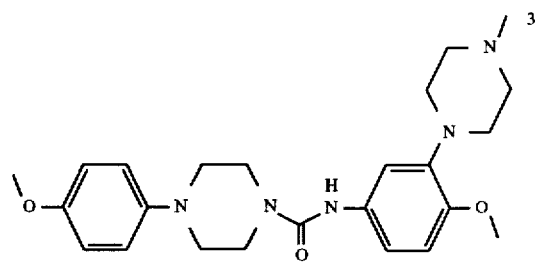

Compound 3 is prepared according to the procedure described in Example 1 using the following reactants: triphosgene (240 mg, 0.81 mmol); 4-methoxy-3-(4-methylpiperazin-1-yl)aniline (490 mg, 2.22 mmol); triethylamine (2×340 µl, 4.86 mmol); 1-(p-methoxyphenyl)piperazine (523 mg, 2.72 mmol); dioxane (25 ml).

At the end of the reaction, the mixture is diluted with water and then extracted three times with ethyl acetate. The organic phases are combined, washed with saturated sodium chloride solution, dried over sodium sulfate and concentrated.

The crude product is purified by flash chromatography with a mixture (95/5/1) and then (90/9/1) of dichloromethane/methanol/aqueous ammonia.

Mass obtained: 464 mg (yield 48%)

Elemental analysis for: $C_{24}H_{33}N_5O_3 \cdot C_4H_4O_4$ Calculated. C. 60.53; H. 6.71, N. 12.60; Experimental. C. 60.02; H. 6.72; N. 12.45

Mass: 440 ($MH^+$), 248, 193

IR (KBr): 3414, 1717, 1655, 1512

1H NMR (DMSO): 2.39 (s, 3H); 2.70 (m, 4H); 3.02 (m, 8H); 3.57 (m, 4H); 3.71 (s, 3H); 3.75 (s, 3H); 6.59 (s, 2H); 6.81–7.13 (m, 7H); 8.40 (s, 1H).

Melting point: 215° C.

EXAMPLE 4

N-[4-Methoxy-3-(4-methylpiperazin-1-yl)phenyl]-4-(m-methoxyphenyl)piperazin-1-ylamide fumarate

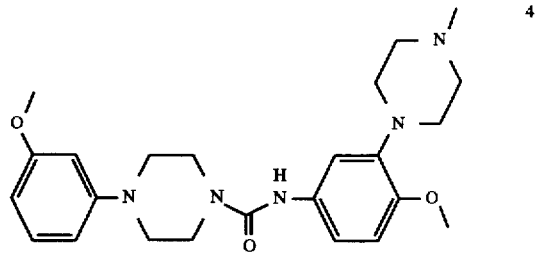

Compound 4 is prepared according to the procedure described in Example 3, using the following reactants: triphosgene (262 mg, 0.88 mmol); 4-methoxy-3-(4-methylpiperazin-1-yl)aniline (531 mg, 2.40 mmol); triethylamine (4×365 µl, 10.55 mmol); 1-(m-methoxyphenyl)piperazine dihydrochloride (636 mg, 2.4 mmol); dioxane (25 ml).

The crude product is purified by flash chromatography with a mixture (90/9/1) of dichloromethane/methanol/aqueous ammonia.

Mass obtained: 390 mg (yield 37%)

Elemental analysis for: $C_{24}H_{33}N_5O_3 \cdot 1.5C_4H_4O_4$ Calculated, C, 58.72; H, 6.41, N, 11.41; Experimental, C, 57.19; H, 6.66; N, 11.70

1H NMR (DMSO): 2.41 (s, 3H); 2.74 (m, 4H); 3.02 (m, 4H); 3.15 (m, 4H); 3.57 (m, 4H); 3.74 (s, 3H); 6.39–6.58 (m, 6H); 6.83 (d, 1H); 7.07–7.18 (m, 3H); 8.41 (s, 1H).

EXAMPLE 5

N-[4-Methoxy-3-(4-methylpiperazin-1-yl)phenyl]-4-(2,3-dimethylphenyl)piperazin-1-ylamide fumarate

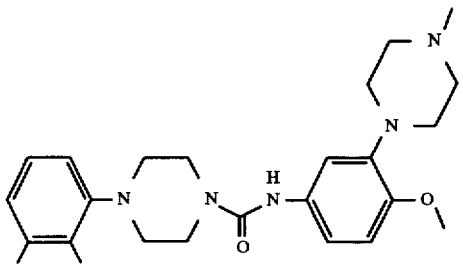

Compound 5 is prepared according to the procedure described in Example 3, using the following reactants: triphosgene (282 mg, 0.95 mmol); 4-methoxy-3-(4-methylpiperazin-1-yl)aniline (567 mg, 2.57 mmol); triethylamine (2×395 μl, 5.70 mmol); 1-(2,3-dimethylphenyl)piperazine (598 mg, 3.14 mmol); dioxane (25 ml).

The crude product is purified by flash chromatography with a mixture (95/5/1) and then (90/9/1) of dichloromethane/methanol/aqueous ammonia.

Mass obtained: 405 mg (yield 36%)

Elemental analysis for: $C_{25}H_{35}N_5O_2 \cdot C_4H_4O_4$ Calculated, C, 62.91; H, 7.10; N, 12.65; Experimental, C, 62.44; H, 7.45; N, 12.26

Mass: 438 (MH$^+$), 248, 191

IR (KBr): 3407, 2949, 1707, 1638, 1500

1H NMR (DMSO): 2.20 (s, 3H); 2.22 (s, 3H); 2.36 (s, 3H); 2.67 (m, 4H); 2.79 (m, 4H); 3.00 (m, 4H); 3.58 (m, 4H); 3.73 (s, 3H); 6.58 (s, 2H); 6.79–7.13 (m, 6H); 8.37 (s, 1H).

Melting point: 133° C.

EXAMPLE 6

N-[4-[4-Methoxy-3-(4-methylpiperazin-1-yl)phenyl]-4-(p-nitrophenyl)piperazin-1-ylamide fumarate

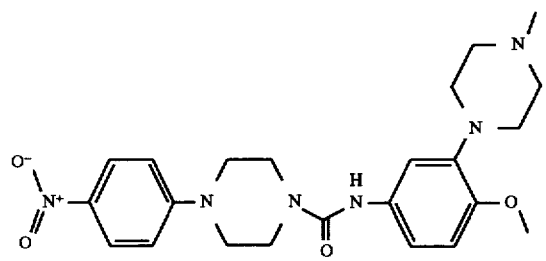

Compound 6 is prepared according to the procedure described in Example 3, using the following reactants: triphosgene (250 mg, 0.85 mmol); 4-methoxy-3-(4-methylpiperazin-1-yl)aniline (510 mg, 2.31 mmol); triethylamine (2×353 μl, 5.10 mmol); 1-(p-nitrophenyl)piperazine (480 mg, 2.31 mmol); dioxane (25 ml).

The crude product is purified by flash chromatography with a mixture (85/14/1) of dichloromethane/methanol/aqueous ammonia.

Mass obtained: 437 mg (yield 42%)

Elemental analysis for: $C_{23}H_{30}N_6O_4 \cdot C_4H_4O_4$ Calculated, C, 56.83; H, 6.01; N, 14.73; Experimental, C, 56.47; H, 5.96; N, 14.50

Mass: 455 (MH$^+$), 248, 208, 178

IR (KBr): 3368, 1692, 1664, 1597, 1510

1H NMR (DMSO): 2.33 (s, 3H); 2.63 (m, 4H); 2.96 (m, 4H); 3.15 (m, 4H); 3.54 (m, 4H); 3.71 (s, 3H); 6.55 (s, 2H); 6.79 (d, 1H); 7.01–7.09 (m, 4H) 8.05 (d, 2H); 8.39 (s, 1H).

Melting point: 215° C.

EXAMPLE 7

N-[4-Methoxy-3-(4-methylpiperazin-1-yl)phenyl]-4-(3,4-methylenedioxy)phenylpiperazin-1-ylamide difumarate

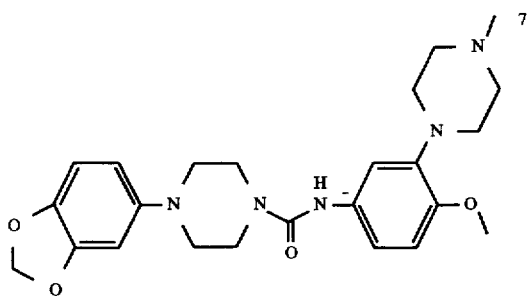

Compound 7 is prepared according to the procedure described in Example 3, using the following reactants: triphosgene (250 mg, 0.83 mmol); 4-methoxy-3-(4-methylpiperazin-1-yl)aniline (510 mg, 2.31 mmol); triethylamine (2×353 μl, 5.10 mmol); 1-(3,4-methylenedioxyphenyl)piperazin (420 mg, 2.04 mmol); dioxane (25 ml).

The crude product is purified by flash chromatography with a mixture (94/6/1) of dichloromethane/methanol/aqueous ammonia.

Mass obtained: 461 mg (yield 50%)

Elemental analysis for: $C_{24}H_{31}N_5O_4 \cdot 2C_4H_4O_4$ Calculated, C, 56.05; H, 5.73; N, 10.21; Experimental, C, 55.46; H, 5.93; N, 9.94

Mass: 454 (MH$^+$), 248, 207, 136

IR (KBr): 3406, 2907, 1707, 1638, 1500

¹H NMR (DMSO): 2.47 (s, 3H); 2.84 (m, 4H); 3.02 (m, 8H); 3.54 (m, 4H); 3.72 (s, 3H); 5.91 (s, 2H); 6.38 (dd, 1H); 6.58 (s, 4H); 6.72–6.83 (m, 3H) 7.06–7.12 (m, 2H); 8.38 (s, 1H).

Melting point: 109° C.

EXAMPLE 8

N-[4-Methoxy-3-(4-methylpiperazin-1-yl)phenyl]-4-(o-cyanophenyl)piperazin-1-ylamide fumarate

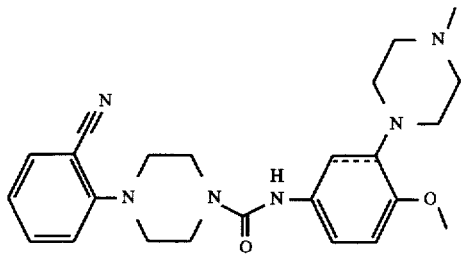

A solution of 4-methoxy-3-(4-methylpiperazin-1-yl)aniline (544 mg, 2.46 mmol) and triethylamine (374 μl, 2.70 mmol) in dioxane (5 ml) is cannulated slowly onto a solution of triphosgene (268 mg, 0.90 mmol) in dioxane (5 ml) under a nitrogen atmosphere. During this operation, the reaction mixture is cooled in an ice bath. It is then returned to room temperature over 20 min before the addition of 1-(o-cyanophenyl)piperazine (460 mg, 2.46 mmol) and triethylamine (374 μl, 2.70 mmol) diluted in dioxane (10 ml). After 2 h at room temperature, the mixture is diluted with water and then extracted three times with ethyl acetate. The organic phases are combined, washed once with saturated sodium chloride solution, dried over magnesium sulfate and concentrated.

The crude product is purified by flash chromatography with a mixture (90/9/1) of dichloromethane/methanol/aqueous ammonia.

Mass obtained: 665 mg (yield 70%)

Elemental analysis for: $C_{24}H_{30}N_6O_2.C_4H_4O_4$ Calculated, C, 61.08; H, 6.22; N, 15.26; Experimental, C, 60.06; H, 6.62; N, 15.14

Mass: 435 (MH+), 248, 188

IR (KBr): 3570, 3389, 1674, 1595

1H NMR (DMSO): 2.35 (s, 3H); 2.67 (m, 4H); 2.97 (m, 4H); 3.14 (m, 4H); 3.59 (m, 4H); 3.71 (s, 3H); 6.54 (s, 2H); 6.79 (d, 1H); 7.04–7.20 (m, 4H); 7.56–7.72 (m, 2H); 8.38 (s, 1H)

Melting point: 141°–143° C.

EXAMPLE 9

N-[4-Methoxy-3-(4-methylpiperazin-1-yl)phenyl]-4-(p-aminophenyl)piperazin-1-ylamide difumarate

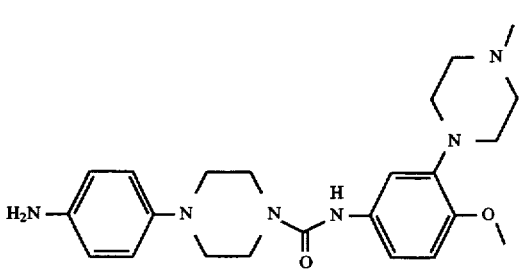

Compound 6 (392 mg, 0.86 mmol) dissolved in methanol (25 ml) is stirred for 4 h at room temperature under a hydrogen atmosphere and in the presence of a catalytic amount of Pd/C. The reaction mixture is then filtered through Celite, concentrated and purified by flash chromatography with a mixture (90/9/1) and then (85/15/1) of dichloromethane/methanol/aqueous ammonia.

Mass obtained: 284 mg (yield 78%)

Elemental analysis for: $C_{23}H_{32}N_6O_2.2C_4H_4O_4$ Calculated, C, 56.70; H, 6.17; N, 12.80; Experimental, C, 56.33; H, 6.40; N, 12.48

IR (KBr): 3418, 1637, 1510

1H NMR (DMSO): 2.48 (s, 3H); 2.88 (m, 8H); 3.05 (m, 4H); 3.54 (m, 4H); 3.74 (s, 3H); 6.50–7.14 (m, 11H); 8.37 (s, 1H).

Melting point: 125° C.

EXAMPLE 10

N-[4-Methoxy-3-(4-methylpiperazin-1-yl)phenyl]-4-(p-methylsulfonylaminophenyl)piperazin-1-ylamide

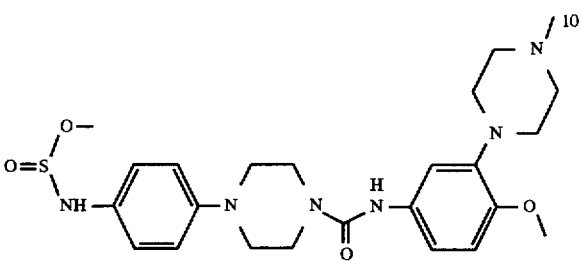

Compound 9 (619 mg, 1.46 mmol) is dissolved in dichloromethane (10 ml) in the presence of triethylamine (300 μl, 2.19 mmol) and cooled to 0° C. Mesyl chloride (135 μl, 0.75 mmol) is added and the reaction mixture is then stirred for 30 minutes at 0° C. and for 4 h at room temperature. After this time, mesyl chloride (135 μl) and triethylamine (300 μl, 2.19 mmol) are added. The reaction mixture is left for a further 30 minutes at room temperature and is then diluted with water. The phases are separated and the aqueous phase extracted twice with dichloromethane. The combined organic phases are washed with saturated sodium chloride solution, dried over magnesium sulfate, filtered and concentrated.

The crude product is purified by flash chromatography with a mixture (95/5/1) and then (9019/1) of dichloromethane/methanol/aqueous ammonia. Two compounds are isolated.

Less polar compound: dimesylation product; 166 mg (yield 19%)

Complete description in Example 11

More polar compound: expected product; 281 mg (yield 38%)

1H NMR (DMSO): 2.23 (s, 3H); 2.46 (m, 4H); 2.89 (s, 3H); 2.95 (m, 4H); 3.13 (m, 4H); 3.58 (m, 4H); 3.74 (s, 3H); 6.81 (d, 1H); 6.97–7.15 (m, 6H); 8.39 (s, 1H); 9.29 (s, 1H).

EXAMPLE 11

N-[4-Methoxy-3-(4-methylpiperazin-1-yl)phenyl]-4-[(p-N,N-bis(methylsulfonyl)aminophenyl]piperazin-1-ylamide

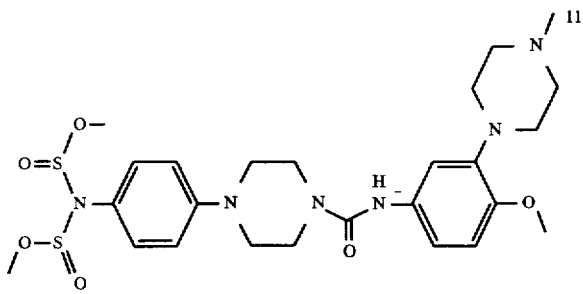

Compound 11 is obtained as a byproduct in the preparation of compound 10. The fumarate is prepared according to the method described previously (in Example 1 for example).

Elemental analysis for: $C_{25}H_{36}N_6O_6S_2 \cdot 0.5 C_4H_4O_1 H_2O$ Calculated, C, 49.38; H, 6.14, N, 12.80; Experimental, C, 48.44; H, 6.10; N, 12.06

IR (KBr): 3418, 1676, 1601, 1510

1H NMR (DMSO): 2.30 (s, 3H); 2.58 (m, 4H); 2.97 (m, 4H); 3.16 (s, 2H, $H_2O$); 3.26 (m, 4H); 3.46 (s, 6H); 3.57 (m, 4H); 3.72 (3H, s); 6.57 (s, 1H) 6.80 (d, 1H); 6.98–7.10 (m, 4H); 7.30 (d, 2H); 8.39 (s, 1H).

Melting point: 160° C.

EXAMPLE 12

2-[4-Methoxy-3-(4-methylpiperazin-1-yl)phenylamino]-1-(4-o-tolylpiperazin-1-yl)ethanone fumarate

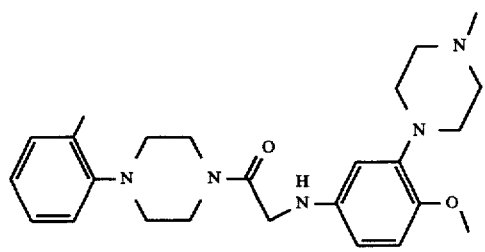

12A: 2-chloro-1-(4-o-tolylpiperazin-1-yl)ethanone

Chloroacetyl chloride (4.5 ml, 56.6 mmol) is added dropwise to a solution of 1-o-tolylpiperazine (8.31 [lacuna], 47.2 mmol) and calcium carbonate (14.2 g, 142 mmol) in methyl ethyl ketone (100 ml) cooled to 0° C. The reaction mixture is stirred at this temperature for 1 h 30 and is then filtered through Celite. The Celite is rinsed several times with ethyl acetate and 3M sodium hydroxide solution. The two phases of the filtrate are then separated and the organic phase is dried over magnesium sulfate, filtered and concentrated to give the expected product in the form of a brown solid.

Mass obtained: 9.9 g (yield 83%)

IR (KBr): 2999, 2945, 1657, 1491, 1433, 1223

1H NMR (DMSO): 2.32 (s, 3H); 2.93 (m, 4H); 3.66 (m, 2H); 3.77 (m, 2H); 4.11 (s, 2H); 6.97–7.25 (m, 4H).

12: A solution of chloride 12A (806 mg; 3.27 mmol), 4-methoxy-3-(4-methylpiperazin-1-yl)aniline (602 mg, 2.72 mmol), sodium carbonate (520 mg, 4.9 mmol) and pyridine (25 μl, 0.3 mmol) in 1-butanol (50 ml) is brought to reflux. After 6 h, the reaction mixture is diluted with water and ethyl acetate. The phases are separated and the aqueous phase is extracted twice with ethyl acetate. The organic phases are then combined, washed with saturated sodium chloride solution, dried over magnesium sulfate, filtered and concentrated.

The crude product is purified by flash chromatography with a mixture (97/3/1) and then (95/5/1) of dichloromethane/methanol/aqueous ammonia.

Mass obtained: 253 mg (yield 21%)

The corresponding fumarate is prepared by addition of 0.9 equivalent of fumaric acid to a solution of the compound in hot methanol. The methanol is evaporated off and the oil obtained is crystallized from ethyl ether.

Elemental analysis for: $C_{25}H_{35}N_5O_2 \cdot C_4H_4O_4$ Calculated, C, 62.91; H, 7.10, N, 12.65; Experimental, C, 61.89; H, 7.09; N, 12.26

Mass: 438 (MH⁺), 222, 177

IR (KBr): 3372, 2922, 2316, 1707, 1655, 1612, 1508

1H NMR (DMSO): 2.26 (s, 3H); 2.35 (s, 3H); 2.64 (m, 4H); 2.84 (m, 4H); 2.99 (m, 4H); 3.65 (m, 7H); 3.87 (s, 2H); 6.19 (d, 1H); 6.31 (s, 1H) 6.57 (s, 2H); 6.68 (d, 1H); 6.96–7.18 (m, 5H).

Melting point: 179° C. (dec.)

EXAMPLE 13

2-[3-(4-methylpiperazin-1-yl)phenoxy-1-(4-o-tolylpiperazin-1-yl)ethanone dihydrochloride

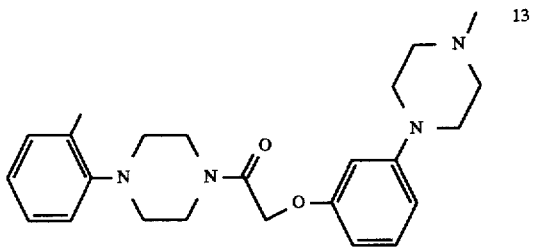

13A: 3-(4-methylpiperazin-1-yl)phenol

3-Aminophenol (2 g, 18 mmol) is brought to the reflux point of 1-butanol (30 ml) in the presence of 2-chloro-N-(chloroethyl)-N-methylethanamine hydrochloride (3.5 g, 18 mmol) and sodium carbonate (95 mg, 9 mmol). After 48 h, the reaction mixture is concentrated and adsorbed on silica and then purified by flash chromatography with a mixture (90/10) of dichloromethane/methanol.

Mass obtained: 574 mg (yield 17%)

1H NMR (DMSO): 2.28 (s, 3H); 2.65 (m, 4H); 3.14 (m, 4H); 6.20–6.42 (m, 3H); 6.96 (dd, 1H); 9.22 (m, 1H).

13: Compounds 13A (529 mg, 2.75 mmol) and 12A (1.04 g, 4.13 mmol) are brought to the reflux point of methyl ethyl ketone (20 ml) in the presence of potassium carbonate (1.26 g, 6.9 mmol) and potassium iodide (55 mg, 0.33 mmol). After 4 h, the reaction mixture is diluted with water and ethyl acetate. The phases are separated and the aqueous phase is then extracted three times with ethyl acetate. The organic phases are combined, washed with saturated sodium chloride solution, dried over magnesium sulfate and concentrated. The crude product obtained is purified by flash chromatography with a mixture (97/3/1) and then (95/5/1) of dichloromethane/methanol/aqueous ammonia.

Mass obtained: 529 mg (yield 47%)

The dihydrochloride is obtained by adding a solution of hydrogen chloride in ethyl ether to a solution of the compound in dichloromethane.

Elemental analysis for: $C_{24}H_{32}N_4O_2 \cdot 2HCl \cdot 0.6H_2O$
Calculated, C, 58.56; H, 7.21; N, 11.38; Cl 14.40
Experimental, C, 58.64; H, 7.47; N, 11.16; Cl 12.53

Mass: 409 (MH$^+$), 219, 193

IR (KBr): 3429, 2928, 2698, 1655, 1603

1H NMR (DMSO): 2.32 (s, 3H); 2.79 (d, 3H); 2.88 (m, 4H); 3.13 (m, 4H); 3.46 (m, 2H); 3.67 (m, 4H); 3.82 (m, 4H); 4.84 (s, 2H); 6.45–6.63 (m, 4H); 6.99–7.23 (m, 5H); 11.22 (m, 1H).

Melting point: 143° C.

EXAMPLE 14

2-[4-Chloro-3-(4-methylpiperazin-1-yl)phenoxy]-1-
[4-(o-tolylpiperazin-1-yl)ethanone

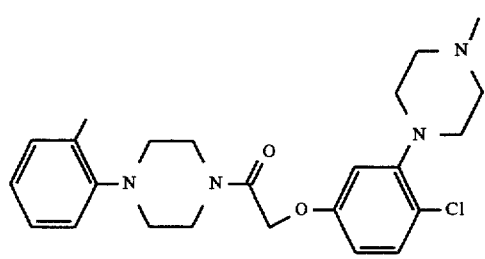

14A: 4-chloro-3-aminophenol

A solution of 4-chloro-3-nitrophenol (2.67 g, 15.4 mmol) in methanol (30 ml) is stirred for 24 h under a hydrogen atmosphere in the presence of a catalytic amount of Pd/C. After this time, the reaction mixture is filtered through Celite and then concentrated. It is purified by flash chromatography with a mixture (95/5/1) and then (90/9/1) of dichloromethane/methanol/aqueous ammonia.

Mass obtained: 1.1 g (yield 66%)

1H NMR (DMSO): 5.16 (m, 2H); 5.97 (dd, 1H); 6.24 (d, 1H); 6.93 (d, 1H); 9.15 (s, 1H).

14B: 4-chloro-3-(4-methylpiperazin-1-yl)phenol Compound 14B is prepared according to the same procedure as 13A, using the following reactants: 14A (1.1 g, 10.1 mmol); 2-chloro-N-(2-chloroethyl)-N-methylethanamine hydrochloride (1.96 g, 10.1 mmol); sodium carbonate (535 mg, 5.05 mmol) in 1-butanol (40 ml).

The crude product obtained is purified by flash chromatography with a mixture (95/5/1) and then (90/9/1) of dichloromethane/methanol/aqueous ammonia.

Mass obtained: 1.1 g (yield 48%)

1H NMR (DMSO): 2.23 (8, 3H); 2.47 (m, 4H); 2.93 (m, 4H); 6.45 (dd, 1H); 6.54 (d, 1H); 7.15 (d, 1H); 9.53 (m, 1H)

14: Compound 14 is prepared according to the same procedure as 13, using the following reactants: compound 12A (660 mg, 2.61 mmol); compound 14B (392 mg, 1.73 mmol); potassium carbonate (600 mg, 4.33 mmol); potassium iodide (30 mg, 0.19 mmol) in methyl ethyl ketone (20 ml).

In this case, the extraction is carried out with dichloromethane instead of ethyl acetate. The crude product is purified by flash chromatography with a mixture (97/3/1) of dichloromethane/methanol/aqueous ammonia.

Mass obtained: 424 mg (yield=55%)

1H NMR (CDCl$_3$): 2.31 (s, 3H); 2.35 (s, 3H); 2.62 (m, 4H); 2.88 (m, 4H); 3.08 (m, 4H); 3.71 (m, 4H); 4.70 (s, 2H); 6.55 (dd, 1H); 6.69 (d, 1E); 6.93–7.27 (m, 5H).

EXAMPLE 15

1-[4-chloro-3-(4-methylpiperazin-1-yl]phenyl 4-o-
tolylpiperazin-1-yloate

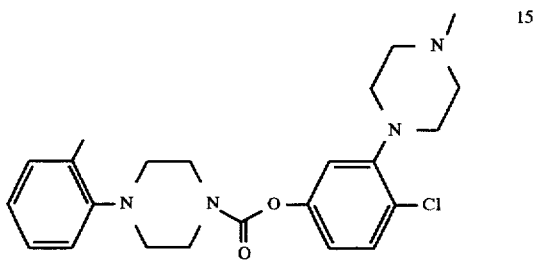

15A: 1-chloroformyl-4-o-tolylpiperazine

A solution of o-tolylpiperazine (1.12 g, 6.4 mmol) and triethylamine (885 µl, 6.4 mmol) in dichloromethane (20 ml) is cannulated onto a solution of triphosgene (700 mg, 2.35 mmol) in dichloromethane at 0° C. and under a nitrogen atmosphere. The reaction mixture is returned to room temperature and stirred for 2 h, then diluted with water. The phases are separated and the aqueous phase is extracted twice with dichloromethane. The combined organic phases are washed with saturated sodium chloride solution, dried over magnesium sulfate, filtered and concentrated.

The crude product is purified by flash chromatography with a mixture (96/4) of petroleum ether/ethyl acetate.

Mass obtained: 738 mg (yield: 48%)

IR (film): 3019, 2920, 2818, 1736

1H NMR (CDCl$_3$): 2.36 (s, 3H); 2.95 (m, 4H); 3.87 (m, 4H); 6.66–7.61 (m, 4H)

15: A solution of 14B (190 mg, 0.84 mmol) in tetrahydrofuran (5 ml) is cannulated onto a suspension of sodium hydride (66%, 37 mg, 0.92 mmol) in tetrahydrofuran (5 ml) at 0° C. and a nitrogen atmosphere. After 15 min, a solution of 15A in tetrahydrofuran (10 ml) is cannulated onto the reaction mixture. This is returned to room temperature and left stirring for 2 h. After this time, it is diluted with water and extracted three times with ethyl acetate. The combined organic phases are then washed with saturated sodium chloride solution, dried over magnesium sulfate, filtered and concentrated.

The crude product is purified by flash chromatography with a mixture (95/5/1) of dichloromethane/methanol/aqueous ammonia.

Mass obtained: 328 mg (yield: 91%) 1H NMR (CDCl$_3$): 2.33 (8, 3H); 2.35 (s, 3H); 2.60 (m, 4H); 295 (m, 4H); 3.09 (m, 4H); 3.75 (m, 4H); 6.73–6.92 (m, 2H); 6.99–7.05 (m, 2H); 7.15–7.34 (m, 3H).

EXAMPLE 16

2-[8-(4-Methylpiperazin-1-yl)naphthalen-2-yloxy]-1-(4-o-tolylpiperazin-1-yl)ethanone

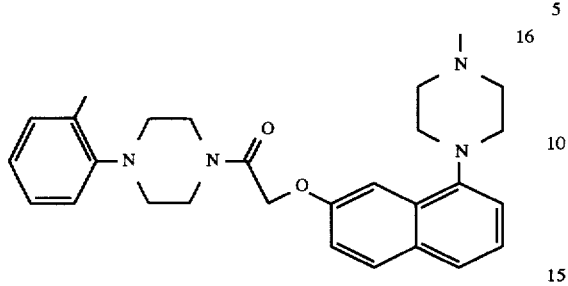

16A: 8-(4-methylpiperazin-1-yl)naphthalen-2-ol

Compound 16A is prepared according to the same procedure as 13A, using the following reactants: 8-aminonaphthalen-2-ol (1.6 g, 10 mmol) 2-chloro-N-(2-chloroethyl)-N-methylethanamine hydrochloride (2 g, 10.4 mmol), sodium carbonate (0.54 g, 5 mmol), 1-butanol (20 ml).

The crude reaction product is purified by flash chromatography with a mixture (95/4/1) and then (90/9/1) of dichloromethane/methanol/aqueous ammonia.

Mass obtained: 1.17 g (yield 48%)

IR (KBr): 3200, 3600, 3073, 2946, 2812, 1622, 1597, 1448

1H NMR (DMSO): 2.28 (s, 3H); 2.58 (m, 4H); 2.96 (m, 4H); 6.98–7.72 (m, 6H); 9.66 (s, 1H).

16: Compound 16 is prepared according to the same procedure as that described previously for the preparation of Example 13 using the intermediates 12A (640 mg, 2.54 mmol), 16A (512 mg, 2.11 mmol), potassium carbonate (35 mg, 0.21 mmol) in methyl ethyl ketone (60 ml).

The crude reaction product is purified by flash chromatography with a mixture (90/9/1) of dichloromethane/methanol/aqueous ammonia.

Mass obtained: 694 mg (yield: 72%)

Elemental analysis for $C_{28}H_{34}N_4O_2$ Calculated: C, 73.33; H, 7.47; N, 12.22; Experimental: C, 72.83; H, 7.44; N, 12.07

IR (KBr): 2938, 2835, 2787, 1668, 1657, 1448

1H NMR (CDCl$_3$): 2.29 (s, 3H); 2.46 (s, 3H); 2.88 (m, 8H); 3.13 (m, 4H); 3.75 (m, 4H); 4.87 (s, 2H); 6.89–7.77 (m, 10H).

EXAMPLE 17

2-[8-(4-Methylpiperazin-1-yl)naphthalen-2-yloxy]-1-[4-(2-cyanophenyl)piperazin-1-yl]ethanone

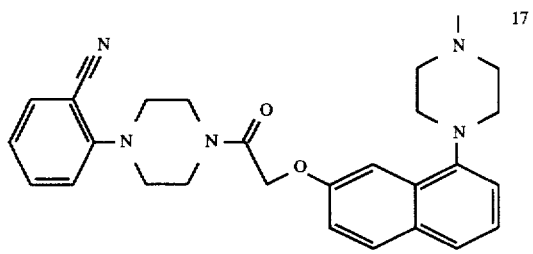

17A: 2-chloro-1-[4-(2-cyanophenyl)piperazin-1-yl] ethanone

Compound 17A is prepared according to the same procedure as that for 12A, using the following reactants: chloroacetyl chloride (670 μl, 8.4 mmol), 1-(2-cyanophenyl)piperazine (1.32 g, 7 mmol), calcium carbonate (2.1 g, 21 mmol), methyl ethyl ketone (30 ml).

Mass obtained: 1.8 g (quantitative yield)

1H NMR (DMSO): 3.14 (m, 4H); 3.64 (m, 4H); 4.44 (s,s 2H); 7.09–7.27 (m, 2H); 7.57–7.74 (m, 2H).

17: Compound 17 is prepared according to the procedure described previously for the preparation of 13, using the following intermediates: 17A (1.04 g, 3.95 mmol), 16A (1.01 g, 4.17 mmol), potassium carbonate (1.36 g, 9.88 mmol), potassium iodide (68 mg, 0.41 mmol), in methyl ethyl ketone (50 ml).

The crude reaction product is purified by flash chromatography with a gradient from (97/3/1) to (90/9/1) of dichloromethane/methanol/aqueous ammonia.

Mass obtained: 925 mg (yield 50%)

1H NMR (CDCl$_3$): 2.45 (s, 3H); 2.76 (m, 4H); 3.21 (m, 8H); 3.87 (m, 4H); 4.90 (s, 2H); 6.95–7.79 (m, 10H).

EXAMPLE 18

2-[8-(4-Methylpiperazin-1-yl)naphthalen-2-yloxy]-1-[4-(4-nitrophenyl)piperazin-1-yl]ethanone.

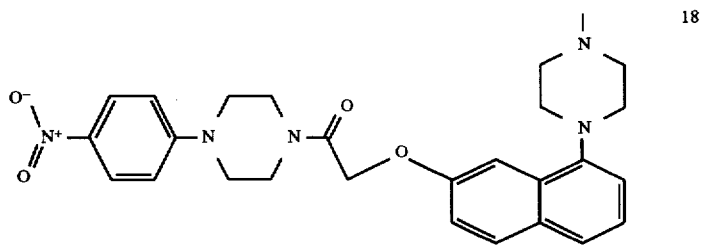

18A: 2-chloro-1-[4-(4-nitrophenyl)piperazin-1-yl] ethanone.

Compound 18A is prepared according to the same procedure as that for 12A, using the following reactants:

chloroacetyl chloride (4.2 ml, 53 mmol), 4-nitrophenylpiperazine (9.18 g, 44.3 mmol), calcium carbonate (13.3 g, 133 mmol), methyl ethyl ketone (100 ml).

In this case, the crude product is purified by flash chromatography with a mixture (97/3) and then (95/5) of dichloromethane/methanol.

Less polar fraction: 3.8 g (yield 30%)

1H NMR (DMSO): 3.35–3.62 (m, 8H); 4.46 (s, 2H); 7.03 (d, 2H); 8.07 (d, 2H).

More polar fraction: 2.12 g

Product of double alkylation (18B) 1,2-bis-|4-(4-nitrophenyl)piperazin-1-yl|ethanone.

Elemental analysis for $C_{22}H_{26}N_6O_5$ Calculated: C, 58.14; H, 5.77; N, 18.49; Experimental: C, 57.94; H, 5.72; N, 18.04

Mass: 455 (MH$^+$)

IR (KBr): 2837, 1647, 1597, 1323

1H NMR (CDCl$_3$): 2.71 (m, 4H); 3.33 (s, 2H); 3.46 (m, 8H); 3.83 (m, 4H); 6.82 (dd, 4H); 8.13 (m, 4H).

18: Compound 18 is prepared according to the procedure described previously for the preparation of 13, using the intermediates 17A (1.75 g, 6 mmol) and 16A (1.21 g, 5 mmol), potassium carbonate (1.7 g, 12.5 mmol) and potassium iodide (83 mg, 0.5 mmol) in methyl ethyl ketone (150 ml).

The crude reaction product is adsorbed onto silica and then purified by flash chromatography with a mixture (97/3/1) of dichloromethane/methanol/aqueous ammonia.

Mass obtained: 111 mg (yield 4%)

1H NMR (CDCl$_3$): 2.43 (s, 3H); 2.76 (m, 4H); 3.12 (m, 4H); 3.45 (m, 4H); 3.84 (m, 4H); 4.90 (s, 2H); 6.80 (d, 2H); 7.11–7.78 (m, 6H); 8.13 (d, 2H).

EXAMPLE 19

8-(4-Methylpiperazin-1-yl)naphthalen-2-yl 4-phenylpiperazin-1-yloate

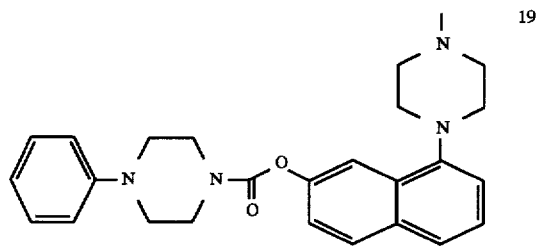

19A: 1-chloroformyl-4-phenylpiperazine

A solution of 1-phenylpiperazine (237 μl, 1.55 mmol) and triethylamine (215 μl, 1.55 mmol) in tetrahydrofuren (10 ml) is added to a solution of triphosgene (155 mg, 0.52 mmol) in tetrahydrofuran (10 ml) at 0° C. and under a nitrogen atmosphere.

The reaction mixture is returned to room temperature. After 30 minutes, it is diluted with water and ethyl acetate. The phases are separated and the aqueous phase is extracted three times with ethyl acetate. The organic phases are then combined, washed with saturated sodium chloride solution, dried over magnesium sulfate, filtered and concentrated.

The crude reaction product is purified by flash chromatography with a mixture (97/3/1) of dichloromethane/methanol/aqueous ammonia.

Mass obtained: 336 mg (yield 96%)

Elemental analysis for $C_{11}H_{14}ClN_2O$ Calculated: C, 58.80; H, 5.83; N, 12.47; Experimental: C, 58.90; H, 5.91; N, 12.30

Mass: 225 (MH$^+$), 189, 163

IR (KBr): 2826, 1728, 1599, 1496, 1410

1H NMR (CDCl$_3$): 3.23 (m, 4H); 3.84 (m, 4H); 6.92–6.99 (m, 3H); 7.27–7.37 (m, 2H).

19: A solution of 16A (205 mg; 0.85 mmol) in tetrahydrofuran (5 ml) is cannulated onto a suspension of sodium hydride (60%, 37 mg, 0.92 mmol) in tetrahydrofuran (5 ml) at 0° C. and under a nitrogen atmosphere. After 15 minutes, the reaction mixture is cannulated onto a solution of 19A (190 mg, 0.85 mmol) in tetrahydrofuran (5 ml) and it is then returned to room temperature and stirred for 15 minutes. The solution is then diluted with water and then extracted three times with ethyl acetate. The organic phases are combined, washed with saturated sodium chloride solution, dried over sodium sulphate, filtered and concentrated. The crude product is purified by flash chromatography with a mixture (95/5/1) of dichloromethane/methanol/aqueous ammonia.

Mass obtained: 301 mg (yield 70%)

The fumarate is prepared by addition of 0.9 equivalent of fumaric acid to a solution of the base in methanol. It is then crystallized from ethyl ether.

Elemental analysis for $C_{26}H_{30}N_4O_2 \cdot 1.3 \times C_4H_4O_4$ Calculated: C, 62.51; H, 6.26; N, 9.35; Experimental: C, 64.95; H, 6.06; N, 9.72

Mass: 431 (MH$^+$), 243, 191, 163, 136

IR (KBr): 3439, 1717, 1597, 1414, 1225

1H NMR (DMSO): 2.39 (s, 3H); 2.78 (m, 4H); 3.05 (m, 4H); 3.24 (m, 4H); 3.62 (m, 2H); 3.79 (m, 2H); 6.58 (s, 2H); 6.79–7.94 (m, 11H).

Melting point: 206° C.

EXAMPLE 20

8-(4-Methylpiperazin-1-yl)naphthalen-2-yl 4-o-tolylpiperazin-1-yloate [sic]

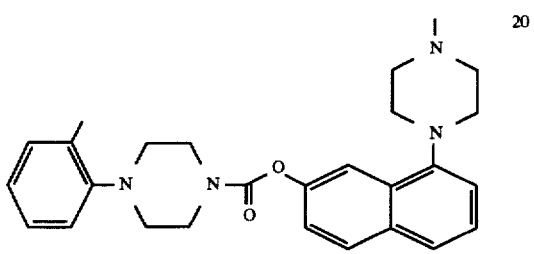

Compound 20 is prepared according to the procedure described previously for the preparation of 15, using 15A (430 mg, 1.8 mmol), 16A (436 mg, 1.8 mmol), sodium hydride (60%, 80 mg, 2 mmol), in tetrahydrofuran (30 ml).

The crude reaction product is purified by flash chromatography with a mixture (95/5/1) of dichloromethane/methanol/aqueous ammonia.

Mass obtained: 664 mg (yield 83%)

1H NMR (CDCl$_3$): 2.36 (s, 3H); 2.42 (s, 3H); 2.72 (m, 4H); 2.98 (m, 4E); 3.14 (m, 4H); 3.80 (m, 4H); 7.00–7.41 (m, 7H); 7.55 (d, 1H); 7.82 (d, 1H); 7.89 (d, 1H1).

EXAMPLE 21

N-|4-Methoxy-3-(4-methylpiperazin-1-yl)phenyl|-4-phenylpiperazin-1-ylamide

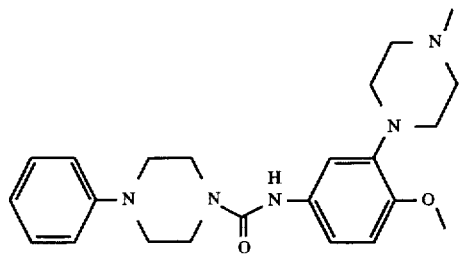

Compound 21 is prepared according to the procedure described in Example 3, using the following reactants: triphosgene (200 mg, 0.68 mmol); 4-methoxy-3-(4-methylpiperazin-1-yl)aniline (447 mg, 2.02 mmol); triethylamine (820 µl, 5.90 mmol); 1-phenylpiperazine (310 ml, 2.02 mmol); tetrahydrofuran (15 ml).

The crude product is purified by flash chromatography with a gradient from (98/2/1) to (90/9/1) of dichloromethane/methanol/aqueous ammonia.

Mass obtained: 92 mg (yield 12%)

This compound is dissolved in methanol and treated with fumaric acid to give the corresponding fumarate. The latter is crystallized from ether.

Elemental analysis for: $C_{23}H_{31}N_5O_2.C_4H_4O_4.H_2O$ Calculated, C, 59.66; H, 6.86; N, 12.88; Experimental, C, 59.62; H, 6.79; N, 12.89

Mass (DCI/NH3): 410 (MH$^+$), 248, 163

IR (KBr): 3395, 2955, 2835, 1707, 1637, 1599, 1500.

1H NMR (DMSO): 2.35 (s, 3H); 2.65 (m, 4H); 2.99 (m, 4H); 3.14 (m, 4H); 3.57 (m, 4H); 3.72 (s, 3H); 6.58 (s, 2H); 6.79–7.27 (m, 8H); 8.39 (s, 1H).

Melting point: 112° C.

EXAMPLE 22

N-|4-Methoxy-3-(4-methylpiperazin-1-yl)phenyl|-4-(1-naphthyl)piperazin-1-ylamide fumarate

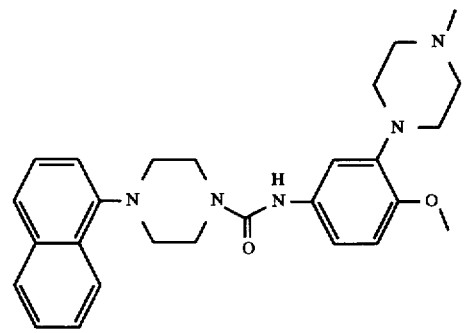

A solution of 4-methoxy-3-(4-methylpiperazin-1-yl) aniline (520 mg, 2.35 mmol) and triethylamine (325 µl, 2.35 mmol) in dichloromethane (10 ml) is cannulated slowly onto a solution of triphosgene (235 mg, 0.78 mmol) in dichloromethane (10 ml) under a nitrogen atmosphere. During this operation, the reaction mixture is cooled in an ice bath. It is then returned to room temperature over 20 min before being cannulated onto a suspension of 1-(1-naphthyl)piperazine (500 mg, 2.35 mmol) and triethylamine (235 µl, 2.35 mmol) in dichloromethane (10 ml). After 2 h at room temperature, the mixture is diluted with water and then extracted three times with ethyl acetate. The organic phases are combined, washed once with saturated sodium chloride solution, dried over magnesium sulfate and concentrated.

The crude product is purified by flash chromatography with a mixture (95/5/1) and then (90/9/1) of dichloromethane/methanol/aqueous ammonia.

Mass obtained: 910 mg (yield 84%)

This compound is dissolved in methanol and treated with fumaric acid to give the corresponding fumarate. The latter is crystallized from ether.

Elemental analysis for: $C_{27}H_{33}N_5O_2.C_4H_4O_4.0.6H_2O$ Calculated, C, 63.49; H, 6.56; N, 11.94; Experimental, C, 63.16; H, 6.65; N, 11.58

Mass (DCI/NH3): 460 (MH$^+$), 248, 213.

IR (KBr): 3375, 1686, 1608, 1500.

1H NMR (DMSO): 2.37 (s, 3H); 2.68 (m, 4H); 3.03 (m, 8H); 3.75 (m, 7M); 6.59 (s, 2H); 6.82 (d, 8.7 Hz, 1H); 6.85–7.19 (m, 3H); 7.41–7.66 (m, 4H); 7.91 (m, 1H); 8.20 (m, 1H); 8.43 (s, 1H).

Melting point: 130° C.

EXAMPLE 23

N-|4-Methoxy-3-(4-methylpiperazin-1-yl)phenyl|-4-(pyridin-4-yl)piperazin-1-ylamide fumarate

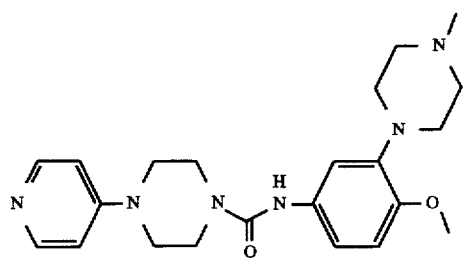

A solution of 4-methoxy-3-(4-methylpiperazin-1-yl) aniline (546 mg, 2.47 mmol) and triethylamine (345 µl, 2.47 mmol) in dichloromethane (10 ml) is cannulated slowly onto a solution of triphosgene (245 mg, 0.82 mmol) in dichloromethane (20 ml) under a nitrogen atmosphere. During this operation, the reaction mixture is cooled in an ice bath. It is then returned to room temperature over 20 min before the addition of 1-(4-pyridyl)piperazine (403 mg, 2.47 mmol) and triethylamine (345 µl, 2.47 mmol) diluted in dichloromethane (10 ml). After 2 h at room temperature, the mixture is diluted with water and the organic phase is washed with saturated sodium chloride solution, dried over magnesium sulfate and concentrated.

The crude product is purified by flash chromatography with a mixture (90/9/1) of dichloromethane/methanol/aqueous ammonia.

Mass obtained: 762 mg (yield 77%)

This compound is dissolved in methanol and treated with fumaric acid to give the corresponding fumarate. The latter is crystallized from ether.

Elemental analysis for: $C_{22}H_{30}N_6O_2.C_4H_4O_4.H_2O$ Calculated, C, 57.82; H, 7.63; N, 15.56; Experimental, C, 57.32; H, 7.06; N, 15.30

Mass (DCI/NH3): 411 (MH$^+$), 248, 222, 164.

IR (KBr) 3306, 1664, 1641, 1535, 1514, 1348, 1250.

1H NMR (DMSO): 2.33 (s, 3H); 2.63 (m, 4H); 2.98 (m, 4H); 3.43 (m, 4H); 3.58 (m, 4H); 3.73 (s, 3H); 6.57 (s, 2H); 6.79–7.12 (m, 5H); 8.20 (d, 6.2 Hz, 2H); 8.72 (s, 1H).

Melting point: 199° C.

EXAMPLE 24

N-[4-Methoxy-3-(4-methylpiperazin-1-yl)phenyl]-4-(pyridin-2-yl)piperazin-1-ylamide fumarate

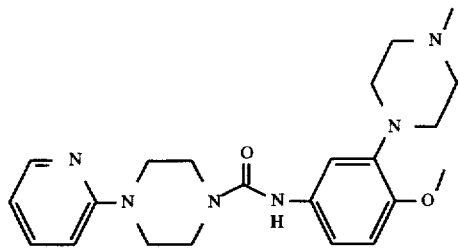

Compound 24 is prepared according to the procedure described in Example 23, using the following reactants: triphosgene (210 mg, 0.71 mmol); 4-methoxy-3-(4-methylpiperazin-1-yl)aniline (481 mg, 2.17 mmol); triethylamine (2×300 μl, 4.34 mmol); 1-(2-pyridyl)piperazine (330 ml, 2.17 mmol); dichloromethane (40 ml).

The crude product is purified by flash chromatography with a mixture (95/5/1) and then (90/9/1) of dichloromethane/methanol/aqueous ammonia.

Mass obtained: 743 mg (yield 83%)

This compound is dissolved in methanol and treated with fumaric acid to give the corresponding fumarate. The latter is crystallized from ether.

Elemental analysis for: $C_{25}H_{35}N_5O_2.C_4H_4O_4.0.37H_2O$ Calculated, C, 58.45; H, 6.74; N, 15.73; Experimental, C, 58.58; H, 6.82; N, 15.24

Mass (DCI/NH3): 411 (MH$^+$), 248, 164.

IR (KBr): 3366, 2837, 1707, 1639, 1595, 1510.

1H NMR (DMSO): 2.36 (s, 3H); 2.67 (m, 4H); 2.99 (m, 4H); 3.52 (m, 8H); 3.73 (s, 3H); 6.58 (s, 2H); 6.67 (dd, 5.0 and 6.9 Hz, 1H); 6.83 (m, 2H); 7.07 (m, 2H); 7.56 (m, 1H); 8.12 (m, 1H); 8.39 (s, 1H).

Melting point: 110° C.

EXAMPLE 25

N-[4-Methoxy-3-(4-methylpiperazin-1-yl)phenyl]-4-(2,6-dimethylphenyl)piperazin-1-ylamide fumarate

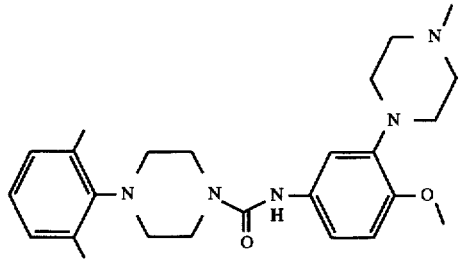

Compound 25 is prepared according to the procedure described in Example 23, using the following reactants: triphosgene (235 mg, 0.79 mmol); 4-methoxy-3-(4-methylpiperazin-1-yl)aniline (525 mg, 2.38 mmol); triethylamine (2×367 μl, 5.24 mmol); 1-(2,6-dimethylphenyl)piperazine (453 mg, 2.38 mmol); dichloromethane (40 ml).

The crude product is purified by flash chromatography with a mixture (95/5/1) and then (90/9/1) of dichloromethane/methanol/aqueous ammonia.

Mass obtained: 656 mg (yield 63%)

This compound is dissolved in methanol and treated with fumaric acid to give the corresponding fumarate. The latter is crystallized from ether.

Elemental analysis for: $C_{25}H_{35}N_5O_2.C_4H_4O_4$ Calculated, C, 62.91; H, 7.10; N, 12.65; Experimental, C, 62.74; H, 7.31; N, 12.86

Mass: (DCI/NH3): 438 (MH$^+$), 294, 248, 191.

IR (KBr): 3366, 2949, 2829, 1701, 1637, 1585, 1510.

12H NMR (DMSO): 2.26 (s, 6H); 2.31 (s, 3H); 2.61 (m, 4H); 2.98 (m, 8H); 3.50 (m, 4H); 3.71 (s, 3H); 6.55 (s, 2H); 6.78 (d, 8.6 Hz, 1H); 6.9–7.10 (m, 5H); 8.31 (s, 1H).

Melting point: 172° C.

EXAMPLE 26

N-[4-Methoxy-3-(4-methylpiperazin-1-yl)phenyl]-4-(5,6,7,8-tetrahydronaphthalen-1-yl)piperazin-1-ylamide fumarate

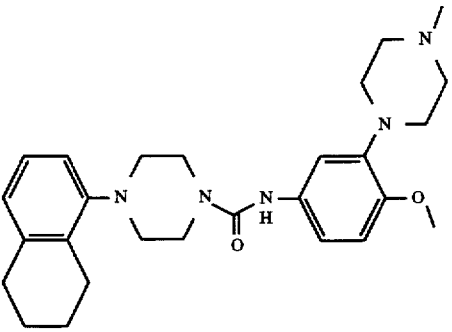

26A: 1-(5,6,7,8-tetrahydronaphthalen-1-yl)piperazine 5,6,7,8-Tetrahydronaphthalen-1-ylamine (1.4 ml, 15 mmol) is brought to the reflux point of 1-butanol (50 ml) in the presence of bis(2-chloroethyl)amine hydrochloride (2.68 g, 15 mmol) and sodium carbonate (800 mg, 7.5 mmol). After 48 h, the reaction mixture is concentrated and impregnated onto silica and then purified by flash chromatography with a mixture (95/5/1) and then (90/9/1) of dichloromethane/methanol/aqueous ammonia.

Mass obtained: 745 mg (yield 22%)

1H NMR (DMSO): 1.68 (t, 3.2 Hz, 4H); 2.67 (t, 6.6 Hz, 4H); 2.81 (t, 4.5 Hz, 4H); 2.97 (t, 3.7 Hz, 4H); 5.33 (se, 2H); 6.83 (m, 2H); 7.04 (m, 1H).

26: Compound 26 is prepared according to the procedure described in Example 23, using the following reactants: triphosgene (181 mg, 0.61 mmol); 4-methoxy-3-(4-methylpiperazin-1-yl)aniline (405 mg, 1.83 mmol); triethylamine (2×253 μl, 3.66 mmol); 1-(5,6,7,8-tetrahydronaphthalen-1-yl)piperazine (26A) (418 mg, 1.83 mmol); dichloromethane (40 ml).

The crude product is purified by flash chromatography with a mixture (95/5/1) of dichloromethane/methanol/aqueous ammonia.

Mass obtained: 799 mg (yield 94%)

This compound is dissolved in methanol and treated with fumaric acid to give the corresponding fumarate. The latter is crystallized from ether.

Elemental analysis for: $C_{27}H_{37}N_5O_2.C_4H_4O_4.0.4H_2O$ Calculated, C, 63.44; H, 7.18, N, 11.93; Experimental, C, 63.54; H, 7.22; N, 12.13

Mass (DCI/NH3): 464 (MH⁺), 294, 248, 217.

IR (KBr): 3414, 2934, 2837, 1637, 1604, 1508.

1H NMR (DMSO): 1.71 (m, 4H); 2.35 (s, 3H); 2.72 (m, 12H); 2.99 (m, 4H); 3.56 (m, 4H); 3.73 (s, 3H); 6.58 (s, 2H); 6.83 (m, 3H); 7.06 (m, 3H); 8.36 (s, 1H).

Melting point: 95° C.

EXAMPLE 27

N-|4-Methoxy-3-(4-methylpiperazin-1-yl)phenyl|-4-(1,2,3,4,5,6-hexamethylphenyl)piperazin-1-ylamide fumarate

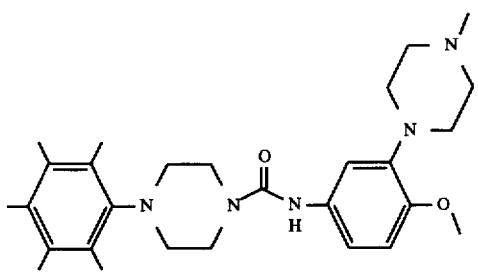

Compound 27 is prepared according to the procedure used for compound 23, starting with 4-methoxy-3-(4-methylpiperazin-1-yl)aniline and 1-(1,2,3,4,5,6-hexamethylphenyl)piperazine.

EXAMPLE 28

N-|4-Methoxy-3-(4-methylpiperazin-1-yl)phenyl|-4-(2,4-dimethylphenyl)piperazin-1-ylamide fumarate

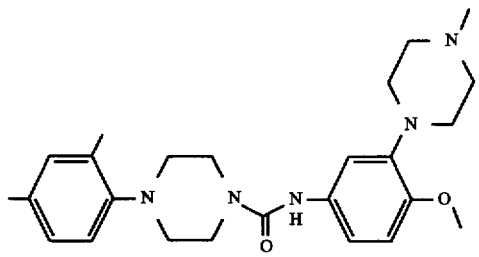

Compound 28 is prepared according to the procedure described in Example 23, using the following reactants: triphosgene (226 mg, 0.76 mmol); 4-methoxy-3-(4-methylpiperazin-1-yl)aniline (504 mg, 2.28 mmol); triethylamine (2×315 μl, 4.56 mmol); 1-(2,4-dimethylphenyl)piperazine (433 mg, 2.28 mmol); dichloromethane (40 ml).

The crude product is purified by flash chromatography with a mixture (95/5/1) of dichloromethane/methanol/aqueous ammonia.

Mass obtained: 230 mg (yield 23%)

This compound is dissolved in methanol and treated with fumaric acid to give the corresponding fumarate. The latter is crystallized from ether.

Elemental analysis for: $C_{25}H_{35}N_5O_2 \cdot C_4H_4O_4 \cdot 0.18H_2O$ Calculated, C, 62.55; H, 7.12; N, 12.58; Experimental, C, 62.22; H, 7.18; N, 12.35

Mass (DCI/NH3): 438 (MH⁺), 248, 191.

IR (KBr): 3339, 2945, 2847, 2810, 1662, 1606, 1510, 1246.

1H NMR (DMSO): 2.20 (s, 3H); 2.23 (8, 3H); 2.33 (s, 3H); 2.63 (m, 4H); 2.77 (m, 4H); 2.97 (m, 4H); 3.54 (m, 4H); 3.71 (s, 3H); 6.56 (s, 2H); 6.79 (d, 8.7 Hz, 1H); 6.92–7.10 (m, 5H); 8.34 (s, 1H).

Melting point: 200° C.

EXAMPLE 29

N-|4-Methoxy-3-(4-methylpiperazin-1-yl)phenyl|-4-(3,4-dimethoxyphenyl)piperazin-1-ylamide fumarate

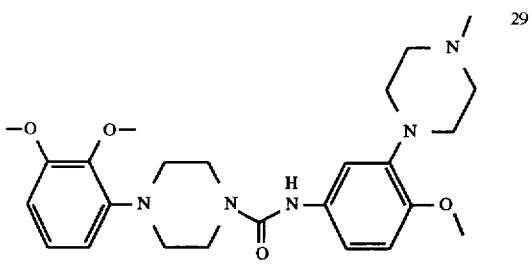

29A: 1-(2,3-dimethoxyphenyl)piperazine:

A solution of butyllithium (26 ml, 1.6M in hexane, 42 mmol) is added dropwise to a solution of piperazine (3.446 g, 40 mmol) in tetrahydrofuran (50 ml) maintained at 0° C. The reaction mixture is then returned to room temperature and stirred for 2 h. A solution of 1,2,3-trimethoxybenzene (6.72 g, 40 mmol) in tetrahydrofuran (20 ml) is then added and the mixture is then maintained at reflux for 12 h. After cooling to room temperature, it is finally poured onto 1N hydrochloric acid solution and extracted three times with ethyl acetate. The aqueous phase is then basified with 3N sodium hydroxide solution and extracted three times with ethyl acetate. The latter organic phases are combined, washed once with saturated sodium chloride solution, dried over magnesium sulfate and concentrated. The final purification is carried out by flash chromatography with a mixture (90/9/1) of dichloromethane/methanol/aqueous ammonia.

Mass obtained: 1.63 g (yield 18%)

1H NMR (CDCl₃): 2.02 (s, 1H); 3.03 (m, 8H); 3.82 (s, 3H); 3.83 (s, 3H); 6.57 (m, 2H); 6.94 (t, 4.0 Hz, 1H).

29: Compound 29 is prepared according to the procedure described in Example 23, using the following reactants: triphosgene (240 mg, 0.81 mmol); 4-methoxy-3-(4-methylpiperazin-1-yl)aniline (534 mg, 2.41 mmol); triethylamine (2×333 μl, 4.82 mmol); 1-(2,3-dimethoxyphenyl)piperazine (29A) (538 mg, 2.41 mmol); dichloromethane (40 ml).

The crude product is purified by flash chromatography with a mixture (92/8/1) of dichloromethane/methanol/aqueous ammonia.

Mass obtained: 879 mg (yield 78%)

This compound is dissolved in methanol and treated with fumaric acid to give the corresponding fumarate. The latter is crystallized from ether.

Elemental analysis for: $C_{25}H_{35}N_5O_4 \cdot C_4H_4O_4$ Calculated, C, 59.48; H, 6.71; N, 11.96; Experimental, C, 59.49; H, 6.85; N, 12.12

Mass (DCI/NH3): 470 (MH⁺), 248, 223.

IR (KBr): 3354, 2932, 2849, 1672, 1510, 1234.

1H NMR (DMSO): 2.32 (s, 3H); 2.63 (m, 4H); 2.96 (m, 8H); 3.54 (m, 4H); 3.70 (s, 6H); 3.73 (s, 3H); 6.54 (s, 2H); 6.57 (d, 6.6 Hz, 1H), 6.66–7.09 (m, 5H); 8.33 (s, 1H).

Melting point: 184° C.

EXAMPLE 30

N-|4-Methoxy-3-(4-methylpiperazin-1-yl)phenyl|-4-(benzodioxan-5-yl)piperazin-1-ylamide difumarate

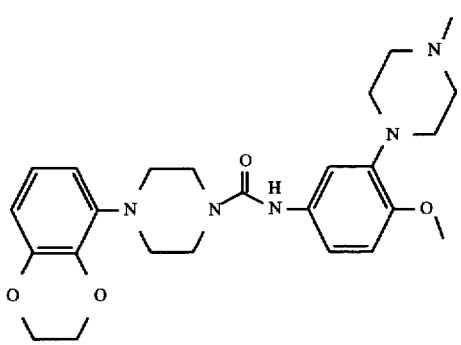

Compound 30 is prepared according to the procedure described in Example 23, using the following reactants: triphosgene (164 mg, 0.55 mmol); 4-methoxy-3-(4-methylpiperazin-1-yl)aniline (370 mg, 1.66 mmol); triethylamine (2×230 μl, 3.32 mmol); 1-(benzodioxan-5-yl)piperazine (EP-0.574.313) (366 mg, 1.66 mmol); dichloromethane (40 ml).

The crude product is purified by flash chromatography with a mixture (92/8/1) and then (90/9/1) of dichloromethane/methanol/aqueous ammonia.

Mass obtained: 613 mg (yield 79%)

This compound is dissolved in methanol and treated with fumaric acid to give the corresponding fumarate. The latter is crystallized from ether.

Elemental analysis for: $C_{25}H_{33}N_5O_4 \cdot 0.6H_2O$ Calculated, C, 58.60; H, 6.48; N, 11.78; Experimental, C, 58.82; H, 6.72; N, 11.29

Mass (DCI/NH$_3$): 468 (MH$^+$), 248, 221, 108.

IR (KBr): 3414, 1637, 1599, 1510.

1H NMR (DMSO): 2.36 (s, 3H); 2.67 (m, 4H); 2.97 (m, 8H); 3.54 (m, 4H); 3.73 (s, 3H); 4.24 (m, 4H); 6.48–6.58 (m, 4H); 6.69–7.11 (m, 2H); 7.06–7.11 (m, 2H); 8.35 (s, 1H).

Melting point: 120°–121° C.

EXAMPLE 31

N-|4-Methoxy-3-(4-methylpiperazin-1-yl)phenyl|-4-(2,4,6-trimethylphenyl)piperazin-1-ylamide fumarate

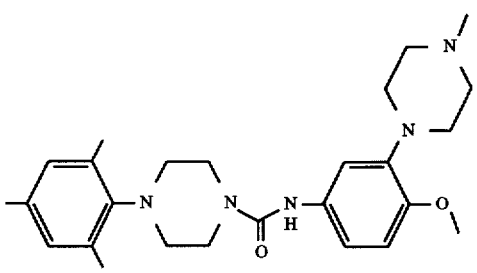

31A: 1-(2,4,6-trimethylphenyl)piperazine

Compound 31A is prepared according to the procedure described for compound 26A, using the following reactants: 2,4,6-trimethylaniline (4.8 ml, 34 mmol); bis(2-chloroethyl)amine hydrochloride (6.05 g, 34 mmol); sodium carbonate (1.8 g, 17 mmol); 1-butanol (75 ml). After impregnating onto silica, the crude reaction product is purified by flash chromatography with a mixture (95/5/1) and then (90/9/1) of dichloromethane/methanol/aqueous ammonia.

Mass obtained: 3.79 g (yield 55%)

1H NMR (CDCl$_3$): 2.23 (s, 3H); 2.29 (s, 6H); 3.01 (m, 8H); 3.33 (se, 1H); 6.81 (s, 2H).

31: Compound 31 is prepared according to the procedure described in Example 23, using the following reactants: triphosgene (218 mg, 0.74 mmol); 4-methoxy-3-(4-methylpiperazin-1-yl)aniline (490 mg, 2.21 mmol); triethylamine (2×305 μl, 4.41 mmol); 1-(2,4,6-trimethylphenyl)piperazine (31A) (450 mg, 2.21 mmol); dichloromethane (40 ml).

The crude product is purified by flash chromatography with a mixture (95/5/1) and then (90/9/1) of dichloromethane/methanol/aqueous ammonia.

Mass obtained: 622 mg (yield 63%)

This compound is dissolved in methanol and treated with fumaric acid to give the corresponding fumarate. The latter is crystallized from ether.

Elemental analysis for: $C_{26}H_{37}N_5O_2 \cdot C_4H_4O_4$ Calculated, C, 63.47; H, 7.28; N, 12.34; Experimental, C, 63.24; H, 7.53; N, 12.52

Mass (DCI/NH3): 452 (MH$^+$), 248, 205.

IR (KBr): 3356, 2949, 2829, 1637, 1518, 1250, 1215.

1H NMR (DMSO): 2.17 (s, 3H); 2.24 (s, 6H); 2.33 (s, 3H); 2.62 (m, 4H); 2.98 (m, 8H); 3.51 (m, 4H); 3.73 (s, 3H); 6.58 (s, 2H); 6.80 (m, 3H); 7.04–7.13 (m, 2H); 8.33 (s, 1H).

Melting point: 171° C.

EXAMPLE 32

N-[4-Methoxy-3-(4-methylpiperazin-1-yl)phenyl]-4-(p-acetylaminophenyl)piperazin-1-ylamide fumarate

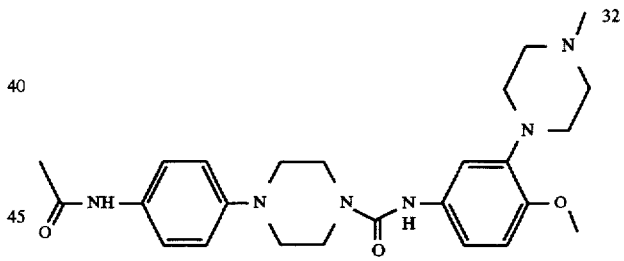

Acetic anhydride (250 ml, 2.65 mmol) is added to a solution of compound 9 (634 mg, 1.49 mmol) in pyridine (20 ml) at 0° C. The reaction mixture is then returned to room temperature and stirred for 12 h. The pyridine is evaporated off and the crude product is then diluted in toluene and evaporated again before being impregnated onto silica and purified by flash chromatography with a mixture (95/5/1) of dichloromethane/methanol/aqueous ammonia.

Mass obtained: 538 mg (yield 77%)

Elemental analysis for: $C_{25}H_{34}N_6O_3 \cdot C_4H_4O_4 \cdot H_2O$ Calculated, C, 57.99; H, 6.71; N, 13.99; Experimental, C, 58.01; H, 6.84; N, 13.88

Mass (DCI/NH3): 467 (MH$^+$), 248, 220, 177.

IR (KBr): 3364, 1643, 1604, 1514.

1H NMR (DMSO): 2.01 (s, 3H); 2.38 (s, 3H); 2.69 (m, 4H), 3.05 (m, 4H); 3.18 (s, H2O); 3.57 (m, 4H); 3.74 (s, 3H); 6.59 (s, 2H); 6.80–7.14 (m, 5H); 7.45 (d, 8.9 Hz, 2H); 8.40 (s, 1H); 9.73 (s, 1H).

Melting point: 178° C.

EXAMPLE 33

N-|4-Methoxy-3-(piperazin-1-yl)phenyl|-4-(2,3-dimethylphenyl)piperazin-1-ylamide hemifumurate

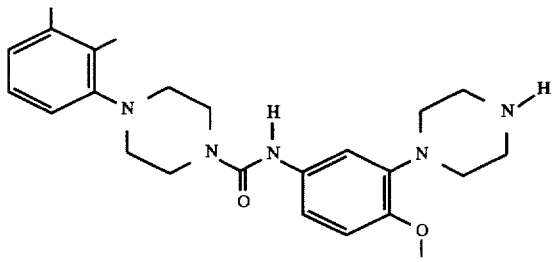

33A: 2-(piperazin-1-yl)-4-nitroanisole 2-(Piperazin-1-yl)anisole (5.1 g; 26 mmol) is acidified slowly with 6 ml of sulfuric acid (5N) and then dehydrated by evaporation under reduced pressure. Concentrated sulfuric acid is then added (22 ml) very slowly (25 min) and the reaction medium is stirred until a homogeneous mixture is obtained. Potassium nitrate (3.1 g; 31 mmol) is added portionwise over 35 minutes. The reaction is stirred for 4 hours. The solution is then poured onto ice and neutralized by addition of sodium carbonate (to pH≈7–8). The nitro derivative is extracted from the aqueous phase with ethyl acetate (4×80 ml), dried over magnesium sulfate and purified by flash chromatography with an eluent gradient (2 to 5% methanol in dichloromethane in the presence of 0.5% aqueous ammonia).

Mass obtained: 5.7 g (93%)

$^1$H NMR (200 MHz, dmso-$d_6$) d: 7.90 (dd, 1H, 2.8 and 9 Hz); 7.62 (d, 1H, 2.8 Hz); 7.14 (d, 1H, 9 Hz); 3.93 (s, 3H); 2.93 (brs, 4H); 2.83 (brs, 4H).

33B: 2-(N-tert-butoxycarbonylpiperazin-1-yl)-4-nitroanisole

The amine 33A (5.7 g; 24 mmol) is dissolved in dichloromethane (48 ml) under an inert atmosphere of nitrogen at room temperature in the presence of triethylamine (3.7 ml; 26 mmol). Di-tert-butyl dicarbonate (5.7 g; 26 mmol) is added slowly, diluted in dichloromethane. The reaction is immediate. The reaction mixture is diluted in dichloromethane, washed with saturated ammonium chloride solution and dried over magnesium sulfate. Compound 33B is purified by filtration through silica, eluting thoroughly with pure dichloromethane (to remove the residual di-tert-butyl dicarbonate) and then with a 3% solution of methanol in dichloromethane.

Mass obtained: 5.1 g (60%)

$^1$H NMR (200 MHz, DMSO-$d_6$) d: 7.93 (dd, 1H, 2.8 and 9 Hz); 7.62 (d, 1H, 2.8 Hz); 7.15 (d, 1H, 9 Hz); 3.93 (s, 3H); 3.43 (brs, 4H); 2.97 (brs, 4H); 1.41 (s, 9H).

33C: 2-(N-tert-butoxycarbonylpiperazin-1-yl)-4-aminoanisole

Compound 33B (5.1 g; 15 mmol) is dissolved in ethanol (48 ml) under an inert atmosphere of nitrogen in the presence of a catalytic amount of Raney nickel. Hydrazine (3.6 ml) is added slowly, prediluted in a little ethanol. The reaction is heated at 50° C. for 3 hours and the solvent is evaporated off under reduced pressure. The aniline is purified by flash chromatography with a mixture of eluents (aqueous ammonia/methanol/dichloromethane=1/5/95).

Mass obtained: 3.9 g (83%)

$^1$H NMR (200 MHz, DMSO-$d_6$) d: 6.62 (d, 1H, 8 Hz); 6.25–6.10 (m, 2H); 4.56 (s, 2H, NH$_2$); 3.64 (s, 3H); 3.42 (brs, 4H); 2.83 (brs, 4H); 1.41 (s, 9H).

33D: N-|4-Methoxy-3-(4-tert-butoxycarbonylpiperazin-1-yl)phenyl|-4-(2,3-dimethylphenyl)piperazin-1-ylamide Derivative 33D is prepared according to the same procedure described for 23, using the following reactants: 33C (1 g; 3.2 mmol); 1-(2,3-xylyl)piperazine (912 mg; 4.8 mmol); triethylamine (0.9 ml; 6.5 mmol); triphosgene (318 mg; 1 mmol); dichloromethane (25 ml).

Mass obtained: 1.1 g (65%)

$^1$H NMR (200 MHz, DMSO-$d_6$) d: 8.34 (s, 1H, NH); 7.15–6.7 (m, 6H); 3.71 (s, 3H); 3.54 (brs, 4H); 3.42 (brs, 4H); 2.84 (brs, 4H); 2.76 (brs, 4H); 2.19 (s, 3H); 2.17 (s, 3H); 1.35 (s, 9H).

33: Derivative 33D (1.1 g; 2.1 mmol) is dissolved in 60 ml of dichloromethane under an inert atmosphere of nitrogen at room temperature and trifluoroacetic acid (10.2 ml) is added. The reaction is stirred for 1 hour and then basified with 0.5M sodium hydroxide. The organic phase is washed with saturated sodium chloride solution, dried over magnesium sulfate and evaporated under reduced pressure. The final product is purified by flash chromatography with a gradient of eluents (dichloromethane/methanol/aqueous ammonia from 98/2/0.5 to 96/4/0.5).

Mass obtained: 641 mg (71%)

$^1$H NMR (200 MHz, DMSO-$d_6$) d: 8.36 (s, 1H, NH); 7.15–6.7 (m, 6H); 3.73 (s, 3H); 3.58 (brs, 4H); 3.82 (brs, 12H); 2.23 (s, 3H); 2.21 (s, 3H).

This compound is dissolved in methanol and treated with fumaric acid to give the corresponding fumarate.

$^1$H NMR (200 MHz, DMSO-$d_6$) d: 8.39 (s, 1H, NH); 7.15–6.7 (m, 6H); 6.42 (s, fumarate); 3.73 (s, 3H); 3.58 (brs, 4H); 3.00 (brs, 8H); 2.79 (brs, 4H); 2.22 (s, 3H); 2.20 (s, 3H).

Elemental analysis for: $C_{24}H_{33}N_5O_2 \cdot 0.5\ C_4H_4O_4$ Calculated C=64.84; H=7.32; N=14.54 Found C=64.52; H=7.31; N=14.43

IR (KBr): 3269, 1633, 1604, 1533, 1510, 1473, 1200.

DCI (NH$_3$): 424 (MH$^+$), 191 (base).

Rf: 0.2 (dichloromethane/methanol/aqueous ammonia= 85/15/1)

EXAMPLE 34

N-|4-Methoxy-3-(4-ethylpiperazin-1-yl)phenyl]-4-(2,3-dimethylphenyl)piperazin-1-ylamide fumarate

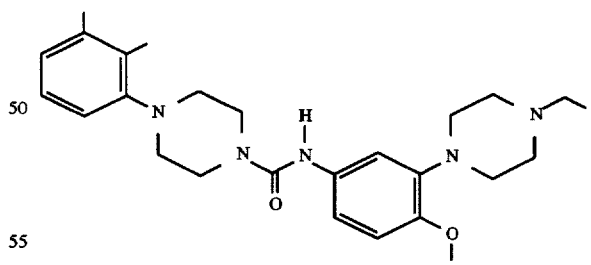

The amine 33 (613 mg, 1.44 mmol) is dissolved in DMF (10 ml) and bromoethane (0.11 ml; 1.44 mmol) is added. Cesium carbonate (470 mg; 1.44 mmol) is introduced and stirring is continued at room temperature for 1 day. The solvent is evaporated off under reduced pressure (<1 mmHg) and the residue is taken up in dichloromethane, washed with saturated sodium bicarbonate solution and dried over magnesium sulfate. The product is purified by flash chromatography with a mixture of methanol (8%) and aqueous ammonia (0.5%) in dichloromethane.

Mass obtained: 427 mg (65%)

This compound is dissolved in methanol and is treated with fumaric acid to give the corresponding fumarate.

$^1$H NMR (200 MHz, DMSO-$d_6$) d: 8.35 (s, 1H, NH); 7.15–6.7 (m, 6H); 6.54 (s, fumarate); 3.71 (s, 3H); 3.56 (brs, 4H); 2.98 (brs, 4H); 2.78 (brs, 4H); 2.63 (brs, 4H); 2.55–2.4 (m, 2H); 2.20 (s, 3H); 2.19 (s, 3H); 1.05 (t, 3H, 7 Hz).

Elemental analysis for: $C_{26}H_{37}N_5O_2 \cdot 0.5C_4H_4O_4 \cdot 0.75$ $H_2O$ Calculated C=64.28; H=7.80; N=13.39 Found C=64.38; H=7.59; N=13.29

IR (KBr): 3431, 1637, 1580, 1541, 1518, 1234.

DCI (NH$_3$): 452 (MH$^+$, base).

Rf: 0.65 (dichloromethane/methanol/aqueous ammonia= 86/14/1)

EXAMPLE 35

N-[4-Methoxy-3-(4-propylpiperazin-1-yl)phenyl]-4-(2,3-dimethylphenyl)piperazin-1-ylamide hemifumarate

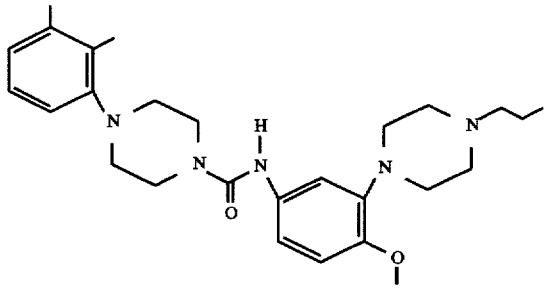

Derivative 35 is prepared according to the same procedure described for 34, using the following reactants: 33 (800 mg; 1.8 mmol); 1-bromopropane (0.16 ml g [sic]; 1.8 mmol); cesium carbonate (586 mg; 1.8 mmol); DMF (13 ml).

Mass obtained: 547 mg (65%)

This compound is dissolved in methanol and treated with fumaric acid to give the corresponding fumarate.

$^1$H NMR (200 MHz, DMSO-$d_6$) d: 8.37 (s, 1H, NH); 7.2–6.75 (m, 6H); 6.57 (s, fumarate); 3.73 (s, 3H); 3.57 (brs, 4H); 2.97 (brs, 4H); 2.79 (brs, 4H); 2.60 (brs, 4H); 2.38 (t, 2H, 7.2 Hz); 2.22 (s, 3H); 2.20 (s, 3H); 1.49 (q, 2H, 7.2 Hz); 0.88 (t, 3H, 7.2 Hz).

Elemental analysis for: $C_{27}H_{39}N_5O_2 \cdot 0.5C_4H_4O_4 \cdot 0.5 H_2O$ Calculated C=65.39; H=7.95; N=13.15 Found C=65.53; H=7.87; N=13.05

IR (KBr): 3300, 2964, 1833, 1643, 1604, 1539, 1508, 1234.

DCI (NH$_3$): 466 (MH$^+$), 276 (base)

Rf: 0.71 (dichloromethane/methanol/aqueous ammonia= 90/10/1)

EXAMPLE 36

2-[3-(4-Methylpiperazin-1-yl)naphthalen-2-yloxy]-1-[4-(2,3-dimethylphenyl)piperazin-1-yl]ethanone fumarate

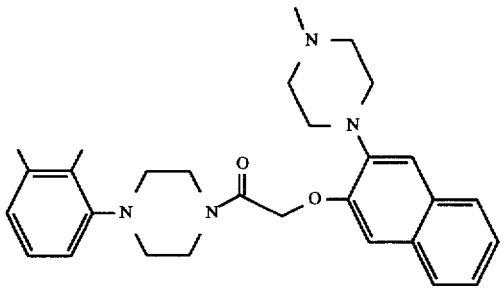

36A: 2-chloro-1-[4-(2,3-xylyl)piperazin-1-yl]-ethanone

Chloroacetyl chloride (1.47 ml, 18.5 mmol) is added dropwise to a solution of 1-(2,3-xylyl)piperazine (3.2 g, 16.8 mmol) and calcium carbonate (5 g, 50 mmol) in methyl ethyl ketone (40 ml) cooled to 0° C. The reaction mixture is stirred at this temperature for 1 h 30 and it is then filtered through Celite. The Celite is rinsed several times with ethyl acetate and 3M sodium hydroxide solution. The two phases of the filtrate are then separated and the organic phase is dried over magnesium sulfate, filtered and concentrated.

Mass obtained: 4.017 g (yield 90%)

1H NMR (CDCl$_3$): 2.24 (s, 3H); 2.27 (s, 3H); 2.87 (m, 4H); 3.67 (m, 4H); 4.11 (s, 2H); 6.75–7.11 (m, 3H).

36B: 3-(4-methylpiperazin-1-yl)naphthalen-2-ol

3-Aminonaphthalen-2-ol (5 g, 31.4 mmol) is brought to the reflux point of 1-butanol (100 ml) in the presence of 2-chloro-N-(chloroethyl)-N-methylethanamine hydrochloride (6.05 g, 31.4 mmol) and sodium carbonate (1.7 g, 16 mmol). After 48 h, the reaction mixture is concentrated and impregnated onto silica and then purified by flash chromatography with a mixture (93/7/1) of dichloromethane/methanol/aqueous ammonia.

Mass obtained: 3.8 g (yield 50%).

1H NMR (DMSO): 2.24 (s, 3H); 2.50 (m, 4H); 3.09 (m, 4H); 7.11 (s, 1H); 7.16–7.27 (m, 3H); 7.57 (m, 1H); 7.66 (m, 1H); 9.65 (s, 1H).

36: Compound 36A (624 mg, 12.75 mmol) and compound 36B (556 mg; 2.29 mmol) are stirred at room temperature under a nitrogen atmosphere in dimethylformamide (15 ml) in the presence of cesium carbonate (1.87 g, 5.73 mmol) for 12 h. The reaction mixture is then diluted with water and extracted three times with ethyl acetate. The organic phases are combined and washed three times with saturated sodium chloride solution, then dried over magnesium sulfate and concentrated. The crude reaction product is purified by flash chromatography with a mixture (95/5/1) and then (90/9/1) of dichloromethane/methanol/aqueous ammonia.

Mass obtained: 827 mg (yield 77%)

Elemental analysis for $C_{29}H_{36}N_4O_4 \cdot C_4H_4O_4$ Calculated: C, 67.33; H, 6.85; N, 9.52; Experimental: C, 67.01; H, 6.89; N, 9.42

IR (KBr): 3433, 2910, 2855, 1710, 1677, 1657, 1479.

1H NMR (DMSO): 2.18 (s, 3H); 2.20 (s, 3H); 2.33 (s, 3H); 2.66 (m, 4H); 2.76 (m, 2H); 2.86 (m, 2H); 3.19 (m, 4H); 3.65 (m, 4H); 4.98 (s, 2H); 6.56 (s, 2H); 6.87 (m, 2H); 7.01 (d, 7.6 Hz, 1H); 7.27 (m, 4H); 7.67 (m, 2H).

Melting point: 186° C.

EXAMPLE 37

2-[2-(4-Methylpiperazin-1-yl)naphthalen-1-yloxy]-1-[4-(2,3-dimethylphenyl)piperazin-1-yl]ethanone fumarate

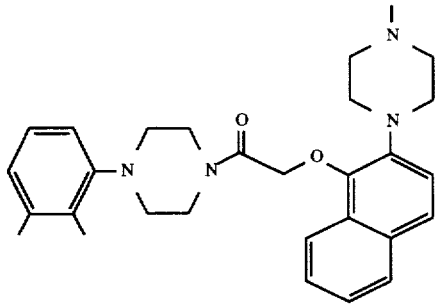

37A: 2-(4-methylpiperazin-1-yl)naphthalon-1-ol

2-Aminonaphthalen-1-ol hydrochloride (3 g, 15.3 mmol) is brought to the reflux point of 1-butanol (150 ml) in the presence of 2-chloro-N-(chloroethyl)-N-methylethanamine hydrochloride (2.95 g, 15.3 mmol) and sodium carbonate (2.44 g, 23 mmol). After 48 h, the reaction mixture is concentrated and impregnated onto silica, then purified by flash chromatography with a mixture (95/5/1) and then (90/9/1) of dichloromethane/methanol/aqueous ammonia Mass obtained: 1.12 g (yield 30%).

1H NMR (CDCl$_3$): 2.38 (s, 3H); 2.67 (m, 4H); 3.02 (m, 4H); 7.20–7.76 (m, 5H); 8.28 (d, 8.3 Hz, 1H).

37: Compound 36A (396 mg, 1.49 mmol) and compound 37A (308 mg; 1.28 mmol) are stirred at room temperature under a nitrogen atmosphere in dimethylformamide (15 ml) in the presence of cesium carbonate (1.03 g, 3.2 mmol) for 12 h. The reaction mixture is then diluted with water and extracted three times with ethyl acetate. The organic phases are combined and washed three times with saturated sodium chloride solution and then dried over magnesium sulfate and concentrated. The crude reaction product is purified by flash chromatography with a mixture (90/9/1) of dichloromethane/methanol/aqueous ammonia.

Mass obtained: 392 mg (yield: 65%)

1H NMR (CDCl$_3$): 2.25 (s, 3H); 2.26 (s, 3H); 2.34 (s, 3H); 2.59 (m, 4H); 2.91 (m, 4H); 3.26 (m, 4H); 3.67 (m, 2H); 3.88 (m, 2H); 4.99 (SAB, 2H); 6.86 (d, 7.8 Hz, 1H); 6.92 (d, 7.1 Hz, 1H); 7.05 (d, 7.7 Hz, 1H); 7.11–7.47 (m, 4H); 8.33 (d, 8.3 Hz, H).

EXAMPLE 38

2-[1-(4-Methylpiperazin-1-yl)naphthalen-2-yloxy]-1-[4-(2,3-dimethylphenyl)piperazin-1-yl]ethanone fumarate

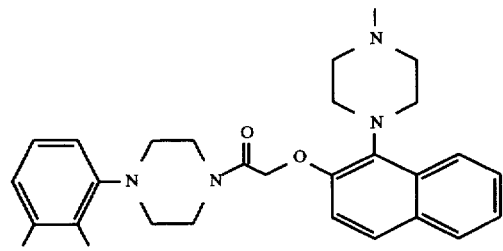

38A: 1-(4-methylpiperazin-1-yl)naphthalen-2-ol

1-Aminonaphthalen-2-ol hydrochloride (5 g, 25.6 mmol) is brought to the reflux point of 1-butanol (100 ml) in the presence of 2-chloro-N-(chloroethyl)-N-methylethanamine hydrochloride (4.9 g, 25.6 mmol) and sodium carbonate (5.4 g, 51 mmol). After 48 h, the reaction mixture is concentrated and impregnated onto silica and then purified by flash chromatography with a mixture (93/7/1) of dichloromethane/methanol/aqueous ammonia.

Mass obtained: 4.35 g (yield 70%)

1H NMR (CDCl$_3$): 2.29 (m, 2H); 2.41 (s, 3H); 2.91 (m, 4H); 3.86 (m, 2H); 7.20–7.42 (m, 3H); 7.62 (d, 8.8 Hz, 1H); 7.76 (d, 8.1 Hz, 1H); 8.03 (d, 8.2 Hz, 1H).

38: Compound 36A (477 mg, 1.79 mmol) and compound 38A (370 mg; 1.52 mmol) are stirred at room temperature under a nitrogen atmosphere in dimethylformamide (15 ml) in the presence of cesium carbonate (1.25 g, 3.82 mmol) for 12 h. The reaction mixture is then diluted with water and extracted three times with ethyl acetate. The organic phases are combined and washed three times with saturated sodium chloride solution and then dried over magnesium sulfate and concentrated. The crude reaction product is purified by flash chromatography with a mixture (90/9/1) of dichloromethane/methanol/aqueous ammonia.

Mass obtained: 615 mg (yield: 86%)

1H NMR (CDCl$_3$): 2.04 (m, 2H); 2.23 (s, 3H); 2.26 (s, 3H); 2.41 (s, 3H); 2.47 (m, 2H); 2.87 (m, 8H); 3.65 (m, 2H); 3.81 (m, 2H); 4.84 (s, 2H); 6.82 (d, 7.8 Hz, 1H); 6.91 (d, 7.1 Hz, 1H); 7.05 (t, 7.7 Hz, 1H); 7.28–7.52 (m, 3H); 7.66 (d, 9.1 Hz, 1H); 7.75 (d, 7.8 Hz, 1H); 8.42 (d, 8.4 Hz, 1H).

EXAMPLE 39

4-(o-Methoxyphenyl)piperazin-1-yloate [4-chloro-3-(4-methylpiperazin-1-yl)phenyl fumarate

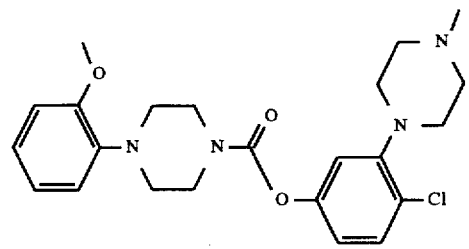

39A: 1-chlorocarbonyl-4-(o-methoxyphenyl)piperazine

Compound 39A is prepared according to the procedure described for compound 15A, using the following reactants: 1-(o-methoxyphenyl)piperazine (441 mg, 2.3 mmol); triphosgene (210 mg, 0.7 mmol); triethylamine (315 ml, 2.3 mmol); tetrahydrofuran (30 ml).

For the treatment, after dilution with water, the reaction mixture is extracted three times with ethyl acetate. The organic phases are combined, washed once with saturated sodium chloride solution, dried over magnesium sulfate and concentrated. The crude product is purified by flash chromatography with a gradient from (98/2/1) to (90/9/1) of dichloromethane/methanol/aqueous ammonia.

Mass obtained: 333 mg (yield 57%)

Mass (DCI/NH3): 255 (MH$^+$).

1H NMR (CDCl$_3$): 3.06 (m, 4H); 3.79 (m, 4H); 3.86 (s, 3H); 6.86–7.08 (m, 4H).

39: Compound 39 is prepared according to the procedure described for compound 15, using the following reactants: compound 14B (316 mg, 1.39 mmol); compound 39A (333 mg, 1.39 mmol); sodium hydride (60%, 67 mg, 1.67 mmol); tetrahydrofuran (35 ml).

The crude product is purified by flash chromatography with a mixture (90/9/1) of dichloromethane/methanol/aqueous ammonia.

Mass obtained: 302 mg (yield 49%)

This compound is dissolved in methanol and treated with fumaric acid to give the corresponding fumarate. The latter is crystallized from ether.

Elemental analysis for: $C_{23}H_{29}ClN_4O_3 \cdot 1.5C_4H_4O_4 \cdot 0.5H_2O$ Calculated, C, 55.46; H, 5.78; N, 8.92; Experimental, C, 55.61; H, 5.68; N, 8.99

Mass (DCI/NH$_3$): 445 (MH$^+$), 411, 371, 221, 193, 136.

IR (KBr): 3433, 2837, 1714, 1595, 1242.

1H NMR (DMSO): 2.34 (s, 3H); 2.64 (m, 4H); 3.02 (m, 8H); 3.57 (m, 2H); 3.71 (m, 2H); 3.80 (s, 3H); 4.41 (very broad —H$_2$O); 6.60 (s, 2H); 6.92 (m, 6H); 7.41 (d, 8.6 Hz, 1H).

Melting point: 105° C. (dec.)

EXAMPLE 40

4-(2,3-Dimethylphenyl)piperazin-1-yloate [4-chloro-3-(4-methylpiperazin-1-yl)]phenyl fumarate

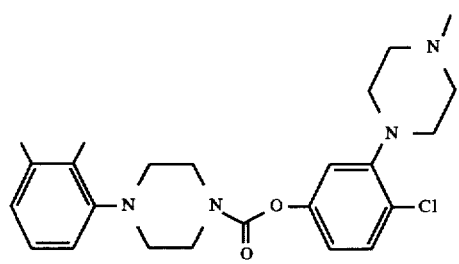

40A: 1-chlorocarbonyl-4-(2,3-dimethylphenyl)piperazine
Compound 40A is prepared according to the procedure described for compound 15A, using the following reactants: 1-(2,3-dimethylphenyl)piperazine (3.94 g, 20.7 mmol); triphosgene (2.05 g, 6.9 mmol); pyridine (1.68 ml, 21 mmol); dichloromethane (150 ml).

The crude product is purified by flash chromatography with dichloromethane.

Mass obtained: 4.067 g (yield 78%)

Elemental analysis for: $C_{13}H_{17}ClN_2O$ Calculated, C, 61.78; H, 6.78; N, 11.08; Cl, 14.03; Experimental, C, 61.76; H, 6.79; N, 10.96; Cl, 14.08.

IR (KBr): 2922, 2824, 1759, 1720, 1406.

1H NMR (CDCl$_3$): 2.25 (s, 3H); 2.29 (s, 3H); 2.92 (m, 4H); 4.15 (m, 4H); 6.87–7.26 (m, 3H).

40: Compound 40 is prepared according to the procedure described for compound 15, using the following reactants: compound 14B (560 mg, 2.47 mmol); compound 40A (624 mg, 2.47 mmol); sodium hydride (60%, 110 mg, 2.72 mmol); tetrahydrofuran (20 ml).

The crude product is purified by flash chromatography with a mixture (95/5/1) of dichloromethane/methanol/aqueous ammonia.

Mass obtained: 1.03 g (yield 94%)

This compound is dissolved in methanol and treated with fumaric acid to give the corresponding fumarate. The latter is crystallized from ether.

Elemental analysis for: $C_{24}H_{31}ClN_4O_2 \cdot 1.2C_4H_4O_4 \cdot 0.15H_2O$ Calculated, C, 59.13; H, 6.22; N, 9.58; Experimental, C, 59.25; H, 6.15; N, 9.43

IR (KBr): 3433, 2916, 1714, 1579.

1H NMR (DMSO): 2.20 (s, 3H); 2.22 (s, 3H); 2.33 (s, 3H); 2.62 (m, 4H); 2.85 (m, 4H); 3.17 (m, 4H); 3.59 (m, 2H); 3.72 (m, 2H); 6.60 (s, 2H); 6.83–7.10 (m, 5H); 7.41 (d, 8.6 Hz, 1H).

Melting point: 150° C.

EXAMPLE 41

4-(2-Fluorophenyl)piperazin-1-yloate [4-chloro-3-(4-methylpiperazin-1-yl)]phenyl fumarate

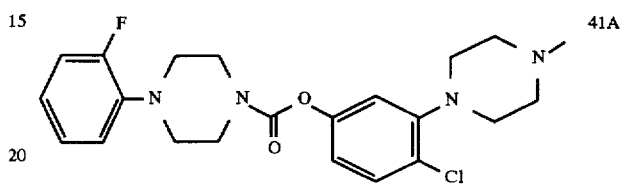

41A: 1-chlorocarbonyl-4-(o-fluorophenyl)piperazine

Compound 41A is prepared according to the procedure described for compound 15A, using the following reactants: 1-(2-fluorophenyl)piperazine (1.54 g, 8.06 mmol); triphosgene (850 mg, 2.85 mmol); pyridine (0.69 ml, 8.6 mmol); dichloromethane (60 ml).

The crude product is purified by flash chromatography with a mixture (90/10) of petroleum ether/ethyl acetate).

Mass obtained: 1.83 g (yield 88%)

Elemental analysis for: $C_{11}H_{12}ClFN_2O$ Calculated, C, 54.44; H, 4.98; N, 11.54; Experimental, C, 54.23; H, 4.96; N, 11.38.

IR (KBr): 3448, 2815, 1731, 1502, 1207.

1H NMR (CDCl$_3$): 3.10 (m, 4H); 3.86 (m, 4H); 6.88–7.12 (m, 4H).

41: Compound 41 is prepared according to the procedure described for compound 15, using the following reactants: compound 14B (934 mg, 4.12 mmol); compound 41A (1.0 g, 4.12 mmol); sodium hydride (60%, 218 mg, 4.54 mmol); tetrahydrofuran (100 ml).

The crude product is purified by flash chromatography with a mixture (95/5/1) of dichloromethane/methanol/aqueous ammonia.

Mass obtained: 1.6 g (yield 90%)

This compound is dissolved in methanol and treated with fumaric acid to give the corresponding fumarate. The latter is crystallized from ether.

Elemental analysis for: $C_{22}H_{26}ClFN_4O_2 \cdot C_4H_4O_4$ Calculated, C, 56.88; H, 5.51; N, 10.21; Cl, 6.46; Experimental, C, 57.01; H, 6.65; N, 9.95; Cl, 6.36

IR (KBr): 2827, 1726, 1711, 1237.

1H NMR (DMSO): 2.31 (s, 3H); 2.59 (m, 4H); 3.00 (m, 8H); 3.59 (m, 2H); 3.72 (m, 2H); 6.59 (s, 2H); 6.85 (dd, 2.6 and 8.5 Hz, 1H); 6.95 (d, 2.6 Hz, 1H); 7.00–7.20 (m, 4H); 7.40 (d, 8.7 Hz, 1H).

Melting point: 177° C.

EXAMPLE 42

[4-chloro-3-(4-methylpiperazin-1-yl)]-4-phenyl (2-naphthyl)piperazin-1-yloate

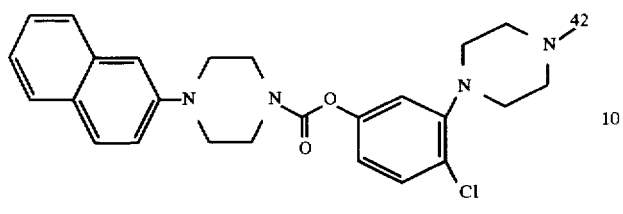

42A: 1-(2-naphthyl)piperazine

Compound 42A is prepared according to the procedure described for compound 13A, using the following reactants: 2-naphthylamine (5 g, 35 mmol); bis(2-chloroethyl)amine hydrochloride (6.23 g, 35 mmol); sodium carbonate (1.85 g, 17 mmol); 1-butanol (100 ml).

The crude product obtained is purified by flash chromatography with a gradient from (95/5/1) to (85/15/1) of dichloromethane/methanol/aqueous ammonia.

Mass obtained: 4.2 g (yield 56%)

Elemental analysis for: $C_{14}H_{16}N_2 \cdot 0.8H_2O$ Calculated, C, 74.17; H, 7.82; N, 32.36; Experimental, C, 74.27; H, 7.68; N, 12.42.

IR (KBr): 3410, 2816, 1620, 1597, 1219.

1H NMR (DMSO): 3.17 (m, 4H); 2.92 (m, 4H), 7.14–7.44 (m, 4H); 7.71–7.77 (m, 3H).

42B: 1-chlorocarbonyl-4-(2-naphthyl)piperazine

Compound 42B is prepared according to the procedure described for compound 15A, using the following reactants: 1-(2-naphthyl)piperazine (600 mg, 2.82 mmol); triphosgene (298 mg, 0.94 mmol); pyridine (230 ml, 2.82 mmol); dichloromethane (20 ml).

The crude product is purified by flash chromatography with a mixture (94/6) of petroleum ether/ethyl acetate.

Mass obtained: 530 mg (yield 68%)

Elemental analysis for: $C_{15}H_{15}ClN_2O \cdot 0.45CH_2Cl_2$ Calculated, C, 59.29; H, 5.12; N, 8.95; Experimental, C, 59.03; H, 5.10; N, 9.01.

1H NMR (CDCL$_3$): 3.34 (t, 5.3 Hz, 4H); 3.94 (m, 4H); 7.16–7.49 (m, 4H); 7.70–7.80 (m, 3H).

42: Compound 42 is prepared according to the procedure described for compound 15, using the following reactants: compound 14B (415 mg, 1.83 mmol); compound 42B (503 mg, 1.83 mmol); sodium hydride (50%, 97 mg, 0.01 [sic] mmol); tetrahydrofuran (45 ml).

The crude product is purified by flash chromatography with a mixture (95/5/1) of dichloromethane/methanol, aqueous ammonia.

Mass obtained: 639 g (yield 75%)

1H NMR (CDCl$_3$): 2.35 (s, 3H); 2.60 (m, 4H); 3.09 (m, 4H); 3.33 (t, 5.0 Hz, 4H); 3.78 (m, 2H); 3.84 (m, 2H); 6.74–6.82 (m, 2H); 7.15–7.45 (m, 5H); 7.68–7.77 (m, 3H).

EXAMPLE 43

[2-(4-methylpiperazin-1-yl)]phenyl 4-(2,3-dimethylphenyl)piperazin-1-yloate

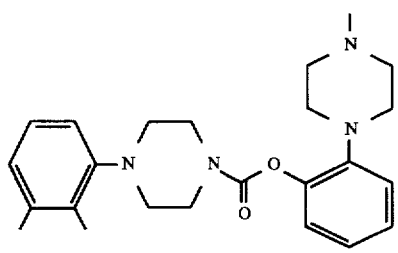

43A: 2-(piperazin-1-yl)phenol

2-Aminophenol (6 g; 54 mmol) is dissolved in 1-butanol (110 ml) in the presence of sodium carbonate (2.9 g; 27.5 mmol) and N-methylbis(2-chloroethyl)amine hydrochloride (11.1 g; 58 mmol). The suspension is heated at 123° C. for 3 days. The butanol is evaporated off under reduced pressure and compound 43A is purified by flash chromatography with the following mixtures of eluents: NH$_4$OH/acetone/CH$_2$Cl$_2$ (0.5/20/80) and then NH$_4$OH/methanol/CH$_2$Cl$_2$(1/5/95).

Mass obtained: 9.09 g (86%)

$^1$H NMR (200 MHz, DMSO-d$_6$) d: 8.95 (brs, 1H, OH); 6.95–6.65 (m, 4H); 2.95 (brs, 4H); 2.48 (brs, 4H); 2.24 (s, 3H).

43: Derivative 43 is prepared according to the same procedure described for 15, using the following reactants: 40A (656 mg; 2.6 mmol); 43A (500 mg; 2.6 mmol); sodium hydride (137 mg; 2.8 mmol); THF (30 ml).

Mass obtained: 741 mg (70%)

$^1$H NMR (200 MHz, DMSO-d$_6$) d: 7.25–6.85 (m, 7H); 3.74 (brs, 2H); 3.59 (brs, 2H); 2.87 (brs, 8H); 2.43 (brs, 4H); 2.21 (s, 3H); 2.19 (s, 6H).

EXAMPLE 44

2-[2-(4-methylpiperazin-1-yl)phenoxy]-1-[4-(2,3-dimethylphenyl)piperazin-1-yl]ethanone hemifumarate

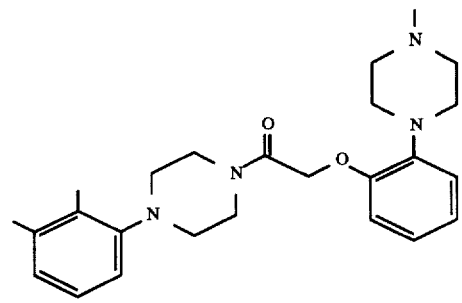

44A: 2-bromo-1-[4-(2,3-dimethylphenyl)piperazin-1-yl] ethanone 1-(2,3-Xylyl)piperazine hydrochloride (5 g; 25 mmol) is suspended in dichloromethane and triethylamine (7.6 ml; 54 mmol) is added. The mixture is cooled to 0° C. and bromoacetyl bromide (2.4 ml; 27 mmol) is added dropwise. The reaction is stirred for 30 minutes and then diluted in dichloromethane, washed with half-saturated sodium bicarbonate solution and dried over magnesium sulfate. The final product is purified by flash chromatography with a gradient of eluents (30/70 to 50/50; EtOAc-Pet. ether).

Mass obtained: 2.5 g (32%)

¹H NMR (200 MHz, DMSO-d₆) d: 7.06 (t, 1H, 7.6 Hz); 7.0–6.85 (m, 2H); 4.44 (s, 2H); 3.61 (brs, 4H); 2.79 (brs, 4H); 2.23 (s, 3H); 2.20 (s, 3H).

44: Compound 43A (800 mg; 4.1 mmol) is dissolved in DMF (9 ml) in the presence of cesium carbonate (4 g; 12.5 mmol) and compound 44A (1.4 g; 4.5 mmol) at room temperature. After stirring for 7 hours, the reaction mixture is diluted in ethyl acetate and washed several times with water. The aqueous phases are combined and extracted once with ethyl acetate. The organic phases are combined and dried over magnesium sulfate. Compound 44 is purified by flash chromatography with a mixture of eluents (1/4/96= NH₄OH/MeOH/CH₂Cl₂).

Mass obtained: 659 mg (37%)

This compound is dissolved in methanol and treated with fumaric acid to give the corresponding fumarate.

¹H NMR (200 MHz, DMSO-d₆) d: 7.15–6.8 (m, 7H); 6.56 (s, fumarate); 4.87 (s, 2H); 3.62 (brs, 4H); 3.06 (brs, 4H); 2.83 (brs, 2H); 2.75 (brs, 2H); 2.59 (brs, 4H); 2.30 (s, 3H); 2.21 (s, 3H); 2.19 (s, 3H).

Elemental analysis for: $C_{25}H_{34}N_4O_2 \cdot 0.5C_4H_4O_4 \cdot 0.5H_2O$
Calculated C=66.23; H=7.62; N=11.44 Found C=66.36; H=7.53; N=11.44

IR (KBr): 3500, 1674, 1657, 1498.

DCI (NH₃): 423 (MH⁺, base)

Rf: 0.56 (dichloromethane/methanol/aqueous ammonia= 90/10/1)

EXAMPLE 45

2-[4-chloro-2-(4-methylpiperazin-1-yl)phenoxy]-1-
[4-(2,3-dimethylphenyl)piperazin-1-yl]ethanone
fumarate

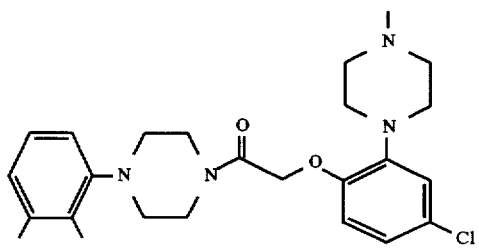

45A: 2-(piperazin-1-yl)-4-chlorophenol

The derivative 45A is prepared according to the same procedure described for 43A, using the following reactants: 2-amino-4-chlorophenol (3 g; 20.9 mmol); N-methylbis(2-chloroethyl)amine hydrochloride (4.2 g; 22 mmol); sodium carbonate (1.1 g; 10.5 mmol); 1-butanol (42 ml).

Mass obtained: 2.8 g (59%)

¹H NMR (200 MHz, DMSO-d₆)d: 9.38 (brs, 1H, OH); 6.9–6.7 (m, 3H); 2.95 (brs, 4H); 2.43 (brs, 4H); 2.20 (s, 3H).

45: Derivative 45 is prepared according to the same procedure described for 44, using the following reactants: 45A (982 mg; 4.3 mmol); 44A (1.3g; 4.3 mmol); cesium carbonate (1.4 g; 4.3 mmol); DMF (15 ml).

Mass obtained: 1.04 g (53%)

This compound is dissolved in methanol and treated with fumaric acid to give the corresponding fumarate.

¹H NMR (200 MHz, DMSO-d6) d: 7.15–6.8 (m, 6H); 6.57 (s, fumarate); 4.90 (s, 2H); 3.59 (brs, 4H); 3.09 (brs, 4H); 2.9–2.7 (m, 4H); 2.64 (brs, 4H); 2.33 (s, 3H); 2.20 (s, 3H); 2.18 (s, 3H).

Elemental analysis for: $C_{25}H_{33}ClN_4O_2 \cdot 1C_4H_4O_4 \cdot 0.25H_2O$
Calculated C=60.31; H=6.54; N=9.70 Found C=60.16; H=6.52; N=9.47

IR (KBr): 3450, 2916, 1709, 1662, 1591, 1498, 1473, 1338, 1219.

DCI (NH₃): 457 (MH⁺, base)

Rf: 0.42 (dichloromethane/methanol/aqueous ammonia= 90/10/08).

EXAMPLE 46

2-[8-(4-methylpiperazin-1-yl)naphthalen-2-yloxy]-1-
[4-(4-aminophenyl)piperazin-1-yl]ethanone
difumarate

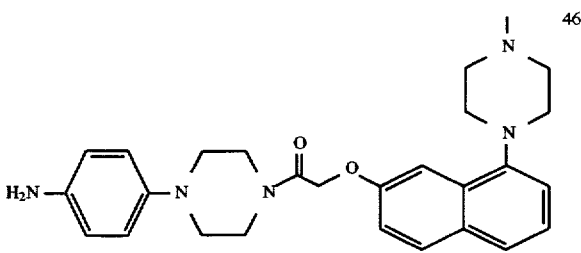

Compound 18 (1.40 g, 2.86 mmol) dissolved in methanol (30 ml) is stirred for 5 days at room temperature under a pressure of 1 atm of hydrogen in the presence of one spatula-ful of Pd/C. The reaction mixture is then filtered through Celite, concentrated and purified by flash chromatography with a mixture (95/5/1) of dichloromethane/methanol/aqueous ammonia.

Mass obtained: 834 mg (yield 63%)

This compound is dissolved in methanol and treated with fumaric acid to give the corresponding fumarate. The latter is crystallized from ether.

Elemental analysis for: $C_{27}H_{33}N_5O_2 \cdot 2C_4H_4O_4$
Calculated, C, 60.77; H, 5.97; N, 10.12; Experimental, C, 61.07; H, 6.28; N, 9.94

Mass (DCI/NH₃): 460 (MH⁺).

IR (KBr): 3427, 2922, 1701, 1637, 1516.

1H NMR (DMSO): 2.41 (s, 3H); 2.86–3.18 (m, 12H); 3.63 (m, 4H); 5.05 (s, 2H); 6.50 (d, 8.7 Hz, 2H); 6.62 (s, 2H); 6.73 (d, 8.7 Hz, 2H); 7.09–7.33 (m, 4H); 7.55 (c, 8.0 Hz, 1H); 7.83 (d, 8.9 Hz, 1H).

Melting point: 101° C.

EXAMPLE 47

2-[8-(4-methylpiperazin-1-yl)naphthalen-2-yloxy]-1-
[4-(4-methylsulfonylaminophenyl)piperazin-1-yl]
ethanone fumarate

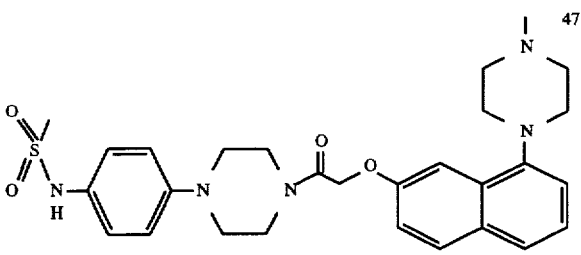

Compound 46 (482 mg, 1.05 mmol) is stirred in pyridine (10 ml) at room temperature and under a nitrogen atmosphere in the presence of mesyl chloride (135 ml, 1.74 mmol) for 4 h. The pyridine is then evaporated off. The crude product is diluted in toluene and evaporated twice in order to remove the pyridine completely. It is then impregnated onto silica and purified by flash chromatography with a mixture (95/5/1) of dichloromethane/methanol/aqueous ammonia.

Mass obtained: 475 mg (yield 84%)

This compound is dissolved in methanol and is treated with fumaric acid to give the corresponding fumarate. The latter is crystallized from ether.

Elemental analysis: $C_{28}H_{35}N_5O_4S \cdot C_4H_4O_4$ Calculated, C, 58.79; H, 6.01; N, 10.71; Experimental, C, 58.39; H, 6.16; N, 10.89

Mass (DCI/NH$_3$): 538 (MH$^+$)

IR (KBr): 3418, 3215, 2922, 2828, 1647, 1512.

1H NMR (DMSO): 2.29 (s, 3H); 2.71 (m, 4H); 2.87 (s, 3H); 3.01–3.21 (m, 8H); 3.65 (m, 4H); 5.06 (s, 2H); 6.60 (s, 2H); 6.94–7.32 (m, 8H); 7.53 (d, 8.1 Hz, 1H); 7.82 (d, 9.0 Hz, 1H); 9.30 (s, 1H).

Melting point: 144°–146° C.

EXAMPLE 48

2-|8-(4-methylpiperazin-1-yl)naphthalen-2-yloxy]-1-|4-(2,3-dimethylphenyl)piperazin-1-yl]ethanone fumarate

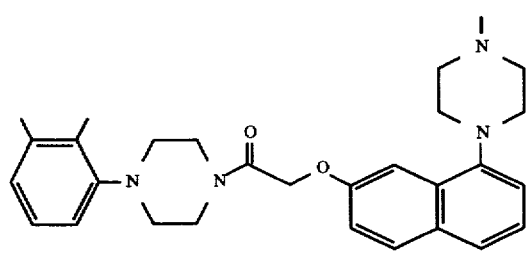

Compound 48 is prepared according to the procedure described for compound 13, using the intermediates 36A (1.07 g, 4.0 mmol), 16A (800 mg; 3.3 mmol), potassium carbonate (1.1 g, 8.3 mmol), and potassium iodide (55 mg, 0.33 mmol) in methyl ethyl ketone (80 ml).

The crude reaction product is purified by flash chromatography with a mixture (95/5/1) of dichloromethane/methanol/aqueous ammonia.

Mass obtained: 1.038 g (yield 67%)

This compound is dissolved in methanol and treated with fumaric acid to give the corresponding fumarate. The latter is crystallized from ether.

Elemental analysis for: $C_{29}H_{36}N_4O_2 \cdot 1.5 C_4H_4O_4$ Calculated: C, 65.00; H, 6.55; N, 8.66; Experimental: C, 64.67; H, 6.57; N, 8.66

Mass (DCI/NH$_3$): 473(MH$^+$), 233, 136.

IR (KBr): 3424, 2887, 2833, 1716, 1697, 1651.

1H NMR (DMSO): 2.18 (s, 3H); 2.21 (s, 3H); 2.40 (s, 3H); 2.80 (m, 8H); 3.03 (m, 4H); 3.69 (m, 4H); 5.05 (s, 2H); 6.59 (s, 3H); 6.83–7.32 (m, 7H); 7.35 (d, 9 Hz, 1H); 7.81 (d, 8 Hz, 1H).

Melting point : 178° C.

EXAMPLE 49

2-|8-(4-methylpiperazin-1-yl)naphthalen-2-yloxy|-1-|4-(1-naphthyl)piperazin-1-yl]ethanone fumarate

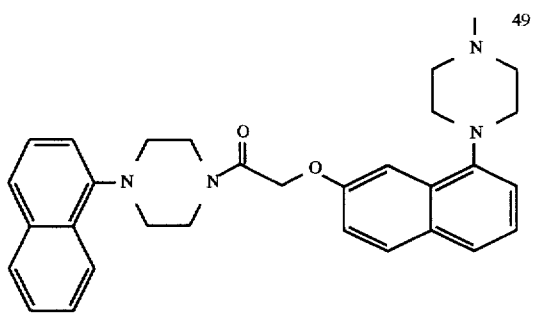

49A: 2-chloro-1-|4-(1-naphthyl)piperazin-1-yl]ethanone

Compound 49A is prepared according to the procedure described for compound 12A using the following reactants: chloroacetyl chloride (270 ml, 3.45 mmol); 1-(1-naphthyl) piperazine (610 mg, 2.88 mmol); calcium carbonate (860 mg, 8.64 mmol); methyl ethyl ketone (20 ml).

Mass obtained: 765 mg (yield 92%)

1H NMR (CDCl$_3$): 3.12 (m, 4H); 3.75 (m, 4H); 4.14 (s, 2H); 7.04 (m, 1H); 7.27–7.63 (m, 4H); 7.85 (m, 1H); 8.22 (m, 1H).

Compound 49 is prepared according to the procedure described for compound 13, using the intermediates 49A (712 mg, 2.46 mmol), 16A (375 mg; 1.55 mmol), potassium carbonate (536 mg, 3.88 mmol) and potassium iodide (25 mg, 0.15 mmol) in methyl ethyl ketone (20 ml).

The crude reaction product is purified by flash chromatography with a mixture (97/3/1) of dichloromethane/methanol/aqueous ammonia.

Mass obtained: 393 mg (yield 51%)

This compound is dissolved in methanol and treated with fumaric acid to give the corresponding fumarate. The latter is crystallized from ether.

Elemental analysis for $C_{31}H_{34}N_4O_2 \cdot C_4H_4O_4 \cdot H_2O$ Calculated: C, 66.86; H, 6.41; N, 8.91; Experimental: C, 67.13; H, 6.30; N, 8.85

Mass (DCI/NH3): 495 (MH$^+$), 255, 243.

IR (KBr): 3429, 3051, 2953, 2826, 1701, 1637, 1448.

1H NMR (DMSO): 2.36 (s, 3H); 2.76 (m, 4H); 3.10 (m, 8H); 3.81 (m, 4H); 5.06 (s, 2H); 6.57 (s, 2H); 7.06–8.19 (m, 13H).

Melting point: 118° C.

EXAMPLE 50

2-[8-(4-methylpiperazin-1-yl)naph-thalen-2-yloxy]-1-[4-(2,3-dimethoxyphenyl)piperazin-1-yl]ethanone

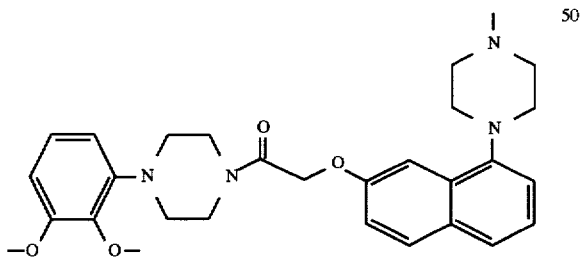

50A: 2-chloro-1-[4-(2,3-dimethoxyphenyl)piperazin-1-yl]ethanone

Compound 50A is prepared according to the procedure described for compound 12, using the following reactants: chloroacetyl chloride (150 ml, 1.87 mmol); 1-(2,3-dimethoxyphenyl)piperazine (29A) (416 mg, 1.87 mmol); potassium carbonate (645 mg, 4.67 mmol); methyl ethyl ketone (20 ml).

Mass obtained: 540 mg (yield 98%)

50: Compound 50A (540 mg, 1.8 mmol) and compound 16A (360 mg; 1.5 mmol) are stirred at room temperature under a nitrogen atmosphere in dimethyl formamide (20 ml) in the presence of cesium carbonate (1.4 g, 4.5 mmol) for 12 h. The reaction mixture is then diluted with water and extracted three times with ethyl acetate. The organic phases are combined and washed three times with saturated sodium chloride solution and then dried over magnesium sulfate and concentrated. The crude reaction product is purified by flash chromatography with a mixture (95/5/1) of dichloromethane/methanol/aqueous ammonia.

Mass obtained: 379 mg (yield 50%)

Elemental analysis for: $C_{29}H_{36}N_4O_4 \cdot 0.22H_2O$ Calculated: C, 68.49; H, 7.22; N, 11.02; Experimental: C, 68.25; H, 7.17; N, 10.84

Mass (DCI/NH3): 505 (MH$^+$),265.

IR (KBr): 3431, 2957, 2828, 2791, 1680, 1595.

1H NMR (CDCl$_3$): 2.44 (s, 3H); 2.77 (m, 4H); 3.13 (m, 8H); 3.82 (m, 10H); 4.87 (s, 2H); 6.49 (d, 8.2 Hz, 1H); 6.63 (d, 8.1 Hz, 1H); 6.92–7.33 (m, 4H); 7.49 (d, 8.0 Hz, 1H); 7.57 (d, 2.4 Hz, 1H); 7.74 (d, 8.9 Hz, 1H).

Melting point: 181° C.

EXAMPLE 51

2-[8-(4-methylpiperazin-1-yl)naphthalen-2-yloxy]-1-[4-(benzodioxan-5-yl)piperazin-1-yl]ethanone fumarate

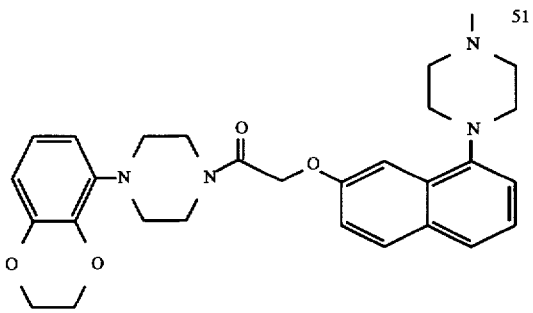

51A: 2-chloro-1-[4-(benzodioxan-5-yl)piperazin-1-yl]ethanone

Compound 53A is prepared according to the procedure described for compound 12A using the following reactants: chloroacetyl chloride (127 ml, 1.6 mmol); 1-benzodioxan-5-yl)piperazine (321 mg, 1.46 mmol); potassium carbonate (504 mg, 3.65 mmol); methyl ethyl ketone (15 ml).

Mass obtained: 368 mg (yield 85%)

Compound 51 is prepared according to the procedure described for compound 50, using the intermediates 51A (368 mg, 1.24 mmol), 16A (300 mg; 1.24 mmol) and cesium carbonate (978 mg, 3.0 mmol) in dimethyl formamide (20 ml).

The crude reaction product is purified by flash chromatography with a mixture (95/5/1) and then (90/9/1) of dichloromethane/methanol/aqueous ammonia.

Mass obtained: 385 mg (yield 62%)

This compound is dissolved in methanol and treated with fumaric acid to give the corresponding fumarate. The latter is crystallized from ether.

Elemental analysis for: $C_{29}H_{34}N_4O_4 \cdot 1.4C_4H_4O_4 \cdot 0.25H_2O$ Calculated: C, 62.06; H, 6.04; N, 8.37; Experimental, C, 61.89; H, 6.04; N, 8.38

Mass (DCI/NH$_3$): 503 (MH$^+$), 263.

IR(KBr): 3431, 1697, 1653.

1H NMR (DMSO): 2.33 (8, 3H); 2.72 (m, 4H); 3.00 (m, 8H); 3.60 (m, 4H); 4.24 (m, 4H); 5.01 (s, 2H); 6.42–6.74 (m, 5.8H); 7.04–7.29 (m, 4H); 7.51 (d, 8.1 Hz, 1H); 7.79 (d, 9.0 Hz, 1H).

Melting point: 206°–207° C.

EXAMPLE 52

2-|8-(4-methylpiperazin-1-yl)naphthalen-2-yloxy|-1-
|4-(2,4,6-trimethylphenyl|piperazin-1-yl)ethanone
fumarate

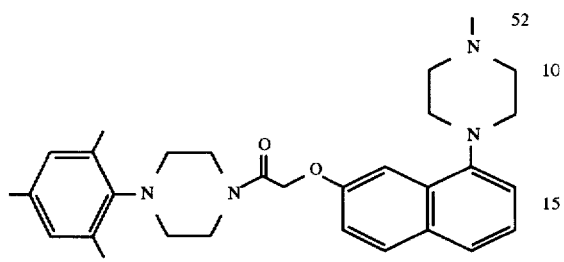

52A: 2-chloro-1-|4-(2,4,6-trimethylphenyl)piperazin-1-yl|ethanone

Compound 52A is prepared according to the procedure described for compound 12A, using the following reactants: chloroacetyl chloride (480 ml, 6.05 mmol); 1-(2,4,6-trimethylphenyl)piperazine (31A) (1.122 g, 5.5 mmol); calcium carbonate (1.65 g, 16.5 mmol); methyl ethyl ketone (25 ml) and dimethylformamide (10 ml) to solubilize the 1-(2,4,6-trimethylphenyl)piperazine).

Mass obtained: 1.49 g (yield 96%).

Compound 52 is prepared according to the procedure described for compound 50, using the intermediates 52A (559 mg, 1.99 mmol), 16A (335 mg; 1.38 mmol) and cesium carbonate (1.13 g, 3.46 mmol) in dimethylformamide (15 ml).

The crude reaction product is purified by flash chromatography with a mixture (95/5/1) of dichloromethane/methanol/aqueous ammonia.

Mass obtained 234 mg (yield 35%)

This compound is dissolved in methanol and treated with fumaric acid to give the corresponding fumarate. The latter is crystallized from ether.

Elemental analysis for $C_{30}H_{38}N_4O_2 \cdot C_4H_4O_4 \cdot 0.85H_2O$
Calculated: C, 66.08; H, 7.13; N, 9.07; Experimental: C, 65.95; H, 7.03; N, 9.09

Mass (DCI/NH$_3$): 487 (MH$^+$), 290, 247, 136.

IR (KBr): 3433, 2918, 1701, 1637, 1448, 1211.

1H NMR (DMSO): 2.16 (s, 3H), 2.19 (s, 6H); 2.40 (s, 3H); 2.75 (m, 4H); 3.03 (m, 8H); 3.57 (m, 4H); 5.04 (s, 2H); 6.59 (s, 2H); 6.78 (s, 2H); 7.07–7.34 (m, 4H); 7.54 (d, 8.0 Hz, 1H); 8.04 (d, 9.0 Hz, 1H).

Melting point: 106° C.

EXAMPLE 53

2-|-(4-methylpiperazin-1-yl)naphthalen-3-yloxy|-1-(4-o-tolypiperazin-1-yl)ethanone fumarate

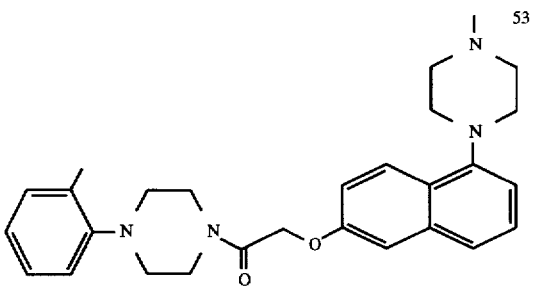

53A: 8-(4-methylpiperazin-1-yl)naphthalen-3-ol

Compound 53A is prepared according to the same procedure as that for 13A, using the following reactants: 8-aminonaphthalen-3-ol (10 g, 62.8 mmol), 2-chloro-N-(2-chlorethyl)-N-methylethananine hydrochloride (11.8 g, 62.8 mmol), sodium carbonate (3.32 g, 31.4 mmol), 1-butanol (200 ml).

The crude reaction product is purified by flash chromatography with a gradient from (98/2/1) to (90/9/1) of dichloromethane/methanol/aqueous ammonia.

Mass obtained: 5.63 g (yield 37%)

1H NMR (DMSO): 2.25 (s, 3H); 2.55 (m, 4H); 2.97 (m, 4H); 6.84 (dd, 1.2 Hz and 7.1 Hz, 1H); 7.07 (m, 2H); 7.30 (m, 2H); 7.94 (d, 9.9 Hz, 1H); 9.68 (s, 1H).

53: Compound 53 is prepared according to the procedure described for the preparation of compound 13, using the intermediates 53A (617 mg, 2.55 mmol), 12A (773 mg; 3.06 mmol), potassium carbonate (880 mg, 6.38 mmol) and potassium iodide (60 mg, 0.37 mmol) in methyl ethyl ketone (80 ml).

The crude reaction product is purified by flash chromatography with a mixture (90/9/1) of dichloromethane/methanol/aqueous ammonia.

Mass obtained: 967 mg (yield 83%)

Elemental analysis for: $C_{28}H_{34}N_4O_2 \cdot C_4H_4O_4$ Calculated: C, 66.88; H, 6.66; N, 9.75; Experimental: C, 66.18; H, 6.78; N, 9.52

Mass (DCI/NH$_3$): 459 (MH$^+$), 219, 177.

IR (KBr): 3431, 2920, 2824, 1707, 1655.

1H NMR (DMSO): 2.29 (s, 3H); 2.43 (s, 3H); 2.82 (m, 8H); 3.07 (m, 4H); 3.66 (m, 4H); 4.99 (s, 2H); 6.60 (s, 2H); 7.00–7.51 (m, 9H); 8.04 (d, 9.2 Hz, 1H).

Melting point: 124° C.

EXAMPLE 54

N-[2-methoxy-3-(4-methylpiperazin-1-yl)phenyl]-4-(2,3-dimethylphenyl)piperazin-1-ylamide fumarate

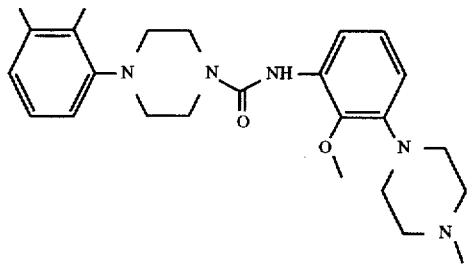

54A: 2-methoxy-3-(4-methylpiperazin-1-yl)aniline

Compound 54A is prepared according to the procedure described for compound 33C, using the following reactants: 2-methoxy-3-(4-methylpiperazin-1-yl)-1-nitrobenzene (3.6 g); hydrazine hydrate (4 ml); ethanol (50 ml); Raney nickel (one spatula-ful). The crude product is purified by flash chromatography with a mixture (90/9/1) of dichloromethane/methanol/aqueous ammonia).

Mass obtained: 2.6 g (yield 67%)

1H NMR (CDCl$_3$): 2.34 (s, 3H); 2.58 (m, 4H); 3.12 (m, 4H); 3.80 (se, 2H) [sic]; 3.84 (s, 3H); 6.33 (dd, 1.4 and 8.0 Hz, 1H); 6.42 (dd, 1.4 and 8.0 Hz, 1H); 6.82 (t, 8.0 Hz, 1H).

Compound 54 is prepared according to the procedure described in Example 23, using the following reactants: triphosgene (282 mg, 0.95 mmol); 2-methoxy-3-(4-methylpiperazin-1-yl)aniline (326 mg, 1.47 mmol); triethylamine (2×206 μl, 2.99 mmol); 1-(2,3-dimethylphenyl)piperazine (304 mg, 1.6 mmol); dichloromethane (25 ml).

The crude product is purified by flash chromatography with a mixture (95/5/1) and then (90/9/1) of dichloromethane/methanol/aqueous ammonia.

Mass obtained: 396 mg (yield 63%)

This compound is dissolved in methanol and treated with fumaric acid to give the corresponding fumarate. The latter is crystallized from ether.

Elemental analysis for: $C_{25}H_{35}N_5O_2$—$C_4H_4O_4$ Calculated, C, 62.91; H, 7.10; N, 12.65; Experimental C, 62.12; H, 7.09; N, 12.49

IR (KBr): 3439, 2822, 1677, 1603, 1529, 1477.

1H NMR (DMSO): 2.21 (s, 3H); 2.23 (s, 3H); 2.33 (s, 3H); 2.63 (m, 4H); 2.82 (m, 4H); 3.05 (m, 4H); 3.60 (m, 4H); 3.80 (s, 3H); 6.60 (s, 2H); 6.65 (dd, 1.2 and 8.0 Hz, 1H); 6.89–7.10 (m, 4H); 7.38 (dd, 1.2 and 8.1 Hz, 1H); 8.10 (s, 1H).

Melting point: 194° C.

BIOLOGICAL RESULTS

Human 5HT$_{1D\alpha}$ and 5HT$_{1D\beta}$ receptors were cloned according to the sequences published by M. Hamblin and M. Metcalf, Mol. Pharmacol., 40, 143 (1991) and Weinshenk et al., Proc. Natl. Acad. Sci. 89, 3630 (1992).

Transitory transfection and permanent transfection of the genes for these receptors was carried out in cell lines Cos-7 and CHO-K$_1$ using an electroporator.

The HeLa HA7 cell line which expresses the human 5HT$_{1A}$ receptor was obtained from Tulco (Duke Univ., Durham, N.C., USA) and cultured according to the method of Fargin et al., J. Biol. Chem 264, 14848 (1989).

The binding of the derivatives of the present invention with the human 5HT$_{1D\alpha}$, 5HT$_{1D\beta}$ and 5HT$_{1A}$ receptors was studied according to the method described by P. Pauwels and C. Palmier (Neuropharmacology, 33, 67, 1994).

The incubation media for these binding measurements comprise 0.4 ml of cell membrane preparation, 0.05 ml of a tritiated ligand [[3H]-5CT (final concentration: 2 nM) for the 5HT$_{1D\alpha}$ and 5HT$_{1D\beta}$ receptors and [3H]-8OH-DPAT (final concentration: 1 nM) for the 5HT$_{1A}$ receptor] and 0.05 ml of the test molecule (final concentrations of 0.1 nM to 1000 nM) or 10 μM (final concentration) of serotonin (5HT$_{1D\alpha}$ and 5HT$_{1D\beta}$) or 1 μM (final concentration) of spiroxatrine (5HT$_{1A}$).

Inhibition of the formation of cyclic AMP (stimulated by forskolin) mediated by the human 5HT$_{1D\beta}$ receptor was studied in CHO-K1 cells transfected with the receptor according to the technique described beforehand for the 5HT$_{1B}$ receptor (P. Pauwels and C. Palmier, Neuropharmacology, 33, 67, 1994).

RESULTS OBTAINED

| Example | 5HT$_{1D\alpha}$ Ki* (nM) | 5HT$_{1D\beta}$ Ki* (nM) | 5HT$_{1A}$ Ki* (nM) | 5HT$_{1D\beta}$ EC**$_{50}$ (nM) |
|---|---|---|---|---|
| 1 | 48 | 2.3 | 396 | >1000 |
| 2 | 68 | 2 | 509 | >1000 |
| 3 | 230 | 8.4 | 1000 | >1000 |
| 5 | 42 | 1.2 | 557 | >1000 |
| 6 | 114 | 5 | 457 | >1000 |
| 7 | 140 | 8.2 | 786 | >1000 |
| 8 | 120 | 11.2 | 714 | >1000 |
| 12 | 420 | 28 | 3000 | >1000 |
| 16 | 0.68 | 0.28 | 50 | >1000 |
| 19 | 2.8 | 0.5 | 16 | >1000 |

*Affinity for the receptors concerned
**Intrinsic agonist acitivity (inhibition of the formation of cyclic AMP induced by forskolin in CHO—K$_1$ cells).

The novel compounds derived from aryl piperazines forming part of the present invention are powerful and selective 5HT$_{1D}$ receptor antagonists, as the examples given above demonstrate. Many compounds forming part of the present invention have the advantage of being particularly selective for human 5HT$_{1D}$ α and β receptors, in particular when compared with the 5HT$_{1A}$, 5HT$_{1C}$, 5HT$_2$, α$_1$, α$_2$ and D$_2$ receptors.

The derivatives of the present invention are also capable of inhibiting the contraction induced by 5-hydroxytryptamine in saphenous rabbit vein rings and for antagonizing the inhibition induced by 5-carboxamidotryptamine (5CT) in the release of serotonin in slices of guinea pig brain.

Another particularly advantageous aspect of the present invention comprises the discovery of antagonists which are selective for human 5HT$_{1D\beta}$ receptor. Indeed, as shown by the pharmacological results described above, many novel compounds corresponding to the general formula (I) have a markedly greater affinity for the 5HT$_{1D\beta}$ receptor when compared with the other receptors including the 5HT$_{1D\alpha}$ receptor. Most of the compounds having this originality which distinguishes them from all the derivatives of the prior art are more precisely defined by a particularly valuable subclass of products of formula (I) which has been defined as corresponding to formula (Ia).

Compounds having a selective antagonist action towards "5HT$_{1-like}$" and/or 5HT$_{1D}$ receptors such as those described in the present invention can exert a beneficial effect on patients suffering from central nervous system disorders. Consequently, the present invention also comprises a method for treating such patients, this method using the administration of an active dose of a compound corresponding to the general formula (I).

The subject of the present invention is also pharmaceutical compositions containing as active principle a compound of general formula I or one of its salts which is acceptable for pharmaceutical use, mixed or combined with a suitable excipient. These compositions may include, for example, the form of solid or liquid compositions, emulsions, lotions or creams.

Solid compositions for oral administration which may be used are tablets, pills, powders (gelatine capsules and cachets) or granules. In these compositions, the active principle according to the invention is mixed with one or more inert diluents, such as starch, cellulose, sucrose, lactose or silica, under a stream of argon. These compositions may also comprise substances other than diluents, for example one or more lubricants such as magnesium stearate or talc, a dye, a coating agent (dragees) or a varnish.

Liquid compositions for oral administration which may be used are pharmaceutically acceptable solutions, suspensions, emulsions, syrups and elixirs containing inert diluents such as water, ethanol, glycerol, plant oils or liquid paraffin. These compositions may comprise substances other than diluents, for example wetting, sweetening, thickening, flavoring or stabilizing products.

The sterile compositions for parenteral administration can preferably be aqueous or non-aqueous solutions, suspensions or emulsions. Water, propylene glycol, a polyethylene glycol, plant oils, in particular olive oil, injectable organic esters, for example ethyl oleate, or other suitable organic solvents, may be used as solvent or vehicle. These compositions may also contain adjuvants, in particular wetting, tonicity, emulsifying, dispersing and stabilizing agents. The sterilization may be carried out in several ways, for example by aseptic filtration, incorporating sterilizing agents into the composition, by irradiation or by heating. The compositions may also be prepared in the form of sterile solid compositions which may be dissolved at the time of use into sterile water or any other injectable sterile medium.

The compositions for rectal administration are suppositories or rectal capsules which contain, besides the active product, excipients such as cocoa butter, semisynthetic glycerides or polyethylene glycols.

The compositions for topical administration may, for example, be creams, lotions, eyedrops, mouthwashes, nasal drops or aerosols.

The doses depend on the desired effect, on the duration of the treatment and on the route of administration used; they are generally between 0.001 g and 1 g (preferably between 0.005 g and 0.25 g) per day preferably via the oral route for an adult, with unit doses ranging from 0.1 mg to 500 mg of active substance, preferably from 1 mg to 50 mg.

In general, the doctor will determine the appropriate dosage according to the age, weight and all the other factors specific to the individual to be treated. The examples which follow illustrate compositions according to the invention.

In the examples of compositions below, the term "reactive component" denotes one or more (generally one) of the compounds of formula (I) according to the present invention:

Tablets

These may be prepared by direct tableting or via wet granulation. The direct tableting procedure is preferred, but it may not be suitable in all cases, depending on the doses and the physical properties of the active component.

| A - by direct tableting | mg for 1 tablet |
| --- | --- |
| active component | 10.0 |
| microcrystalline cellulose BPC | 89.5 |
| magnesium stearate | 0.5 |
| | 100.0 |

The active component is passed through a screen with a mesh size on the side of 250 µm, mixed with the excipients and the mixture is tableted using 6.0 mm punches. Tablets having other mechanical strengths may be prepared by changing the compression weight with the use of suitable punches.

| B - Wet granulation | mg for one tablet |
| --- | --- |
| active component | 10.0 |
| lactose Codex | 74.5 |
| starch Codex | 10.0 |
| pregelatinized cornstarch Codex | 5.0 |
| magnesium stearate | 0.5 |
| tableting weight | 100.0 |

The active component is passed through a screen with a mesh size of 250 µm and is mixed with the lactose, the starch and the pregelatinized starch. The mixed powders are moistened with purified water, made into granules, dried, screened and mixed with magnesium stearate. The lubricated granules are tableted as for the direct tableting formulations. A coating film may be applied to the tablets using suitable film-forming materials, for example methylcellulose or hydroxypropylmethylcellulose, according to standard techniques. The tablets may also be coated with sugar.

Capsules

| Capsules | mg for one capsule |
| --- | --- |
| active component | 10.0 |
| *starch 1500 | 89.5 |
| magnesium stearate | 0.5 |
| Codex filling weight | 100.0 |

*a directly-compressible form of starch obtained from the firm Colorcon Ltd., Orpington, Kent, United Kingdom.

The active component is passed through a screen with a mesh size of 250 µm and is mixed with the other substances. The mixture is introduced into hard No. 2 gelatine capsules on a suitable filling machine. Other dosage units may be prepared by modifying the filling weight and, when necessary, by changing the size of the capsule.

Syrup

| Syrup | mg per 5 ml dose |
| --- | --- |
| active component | 10.0 |
| sucrose Codex | 2750.0 |
| glycerol Codex | 500.0 |

| Syrup | mg per 5 ml dose |
|---|---|
| buffer | q.s. |
| flavoring | |
| dye | |
| preserving agent | |
| distilled water | 5.0 |

The active component, the buffer, the flavoring, the dye and the preserving agent are dissolved in some of the water and the glycerol is added. The remaining water is heated to 80° C., the sucrose is dissolved therein and the solution is then cooled. The two solutions are combined, the volume is adjusted and mixing is carried out. The syrup obtained is clarified by filtration.

Suppositories

| Suppositories | |
|---|---|
| active component | 10.0 mg |
| *Witepsol H15 complement to | 1.0 g |

*Brand marketing for Adeps Solidus of the European Pharmacopeia.

A suspension of the active component in the Witepsol H15 is prepared and is introduced into a suitable machine with 1 g suppository molds.

Liquid for administration by intravenous injection

| | g/l |
|---|---|
| active component | 2.0 |
| water for injection Codex complement to | 1000.0 |

Sodium chloride may be added to adjust the tonicity of the solution and to adjust the pH to the maximum stability and/or to facilitate the dissolution of the active component using a dilute alkali or acid, or by adding suitable buffer salts. The solution is prepared, it is clarified and is introduced into ampules of suitable size which are sealed by melting the glass. The liquid for injection may also be sterilized by heating in an autoclave according to one of the acceptable cycles. The solution may also be sterilized by filtration and introduced into a sterile ampule under aseptic conditions. The solution may be introduced into the ampules under a gas atmosphere.

| Cartridges for inhalation | |
|---|---|
| | g/cartridge |
| micronized active component | 1.0 |
| lactose Codex | 39.0 |

The active component is micronized in a fluid-energy grinder and is rendered into fine particles before mixing with tablet lactose in a high-energy mixer. The pulverulent mixture is introduced into hard No. 3 gelatine capsules on a suitable encapsulating machine. The content of the cartridges is administered using a powder inhaler.

| Pressurized aerosol with a metering valve | |
|---|---|
| | mg/dose for 1 can |
| micronized active component | 0.500 120 mg |
| oleic acid Codex | 0.050 12 mg |
| trichlorofluoromethane for pharmaceutical use | 22.25 5.34 g |
| dichlorodifluoromethane for pharmaceutical use | 60.90 14.62 g |

The active component is micronized in a fluid-energy grinder and is rendered into fine particles. The oleic acid is mixed with the trichlorofluoromethane at a temperature of 10°–15° C. and the micronized medicament is introduced into the solution using a high-shear mixer. The suspension is introduced in measured amount into aluminum aerosol cans onto which suitable metering valves which deliver a dose of 85 mg of the suspension are fixed; the dichlorodifluoromethane is introduced into the cans by injection through the valves.

We claim:

1. A compound corresponding to formula (I)

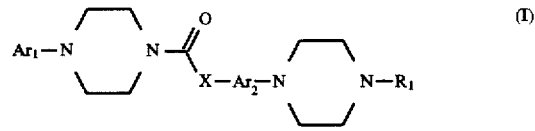

in which

Ar$_1$ represents an aromatic residue selected from the group consisting of phenyl, naphthyl, and pyridyl, and such an aromatic residue substituted with one or more substituents selected from the group consisting of linear and branched alkyl residues having 1 to 6 carbon atoms inclusive, trifluoromethyl, 2,2,2-trifluoroethyl, phenyl, benzyl, hydroxyl (OH), thiol (SH), ether (OR'$_2$), thioether (SR'$_2$), ester (OCOR'$_2$), carbamate (OCONHR$_2$), carbonate (OCO$_2$R'$_2$), carbonyl (COR$_2$, COOR'$_2$, or CONHR$_2$), halogen selected from the group consisting of fluorine, chlorine, bromine, and iodine, amine (NR$_2$R$_3$), nitro (NO$_2$), nitrile (CN), aminocarbonyl (NHCOR'$_2$, NHCO$_2$R'$_2$, or NHCONR$_2$R$_3$), aminosulfonyl (NHSO$_2$R'$_2$, N(SO$_2$R'$_2$)$_2$, NHSO$_2$OR'$_2$, or NHSO$_2$NR$_2$R$_3$), and sulfonyl (SO$_2$R'$_2$ or SO$_2$NR$_2$R$_3$), and X represents O, NH, CH$_2$O, or CH$_2$NH, Ar$_2$ represents an aromatic radical selected from the group consisting of phenyl and naphthyl to which X and the piperazine are attached on different carbons and which is unsubstituted or substituted by a linear or branched alkyl radical having 1 to 6 carbon atoms inclusive, alkoxy (OR$_4$), or halogen selected from the group consisting of chlorine, fluorine, iodine, and bromine, R$_1$, R$_2$, R$_3$ and R$_4$, which are identical or different, represent hydrogen or a linear or branched alkyl having 1 to 6 carbon atoms inclusive, R'$_2$ represents linear or branched alkyl having 1 to 6 carbon atoms inclusive, and their salts, and hydrates, which are physiologically acceptable for therapeutic use, their geometrical and optical isomers and their mixtures in all proportions and in racemic form.

2. A compound according to claim 1 in which $Ar_2$ represents unsubstituted or substituted phenyl corresponding to formula (Ia)

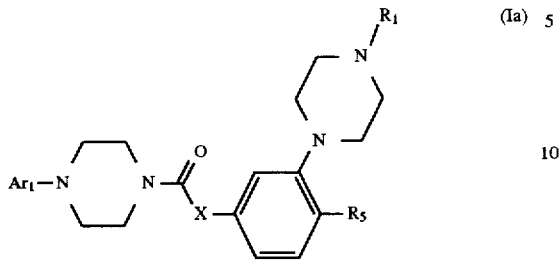

wherein $R_5$ represents hydrogen, linear or branched alkyl having 1 to 6 carbon atoms inclusive, alkoxy ($OR_4$), or halogen selected from the group consisting of chlorine, fluorine, iodine, and bromine, $R_4$ being hydrogen or linear or branched alkyl having 1 to 6 carbon atoms inclusive.

3. A compound according to claim 1 in which $Ar_2$ represents unsubstituted or substituted naphthyl corresponding to the formula (Ib)

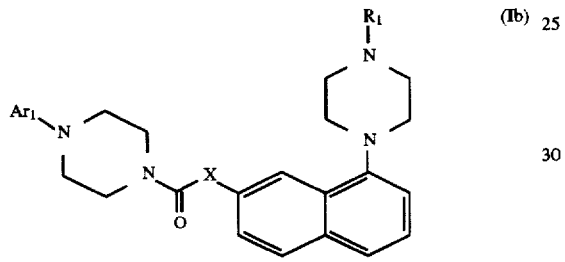

wherein $Ar_1$, X, and $R_1$ are as defined in claim 1.

4. A compound according to claim 1, wherein $R_1$ represents methyl.

5. A compound according to claim 1, wherein $R_1$ represents hydrogen.

6. A compound according to claim 1, wherein $Ar_1$ represents a phenyl substituted with one or more substitutents selected from the group consisting of methyl, methoxy, amine, nitro, nitrile, or halogen selected from the group consisting of Cl, Br, and F.

7. A compound according to claim 1, wherein $Ar_1$ represents a pyridyl radical.

8. A compound according to claim 1, wherein $Ar_1$ represents a naphthyl.

9. A compound according to claim 1, wherein X represents an oxygen atom.

10. A compound according to claim 1, wherein X represents NH.

11. A compound according to claim 1, wherein X represents —$CH_2$—O.

12. A compound according to claim 1, wherein X represents —$CH_2$—NH.

13. A compound according to claim 2, wherein $R_5$ represents $OCH_3$ or Cl.

14. A compound according claim 1 in the form of an acceptable salt for therapeutic use selected from the group consisting of hydrochlorides, hydrobromides, sulfates, methanesulfonates, fumarates, maleates, and succinates.

15. A compound according to claim 2, wherein $R_1$ represents methyl.

16. A compound according to claim 3, wherein $R_1$ represents methyl.

17. A compound according to claim 2, wherein $R_1$ represents hydrogen.

18. A compound according to claim 3, wherein $R_1$ represents hydrogen.

19. A compound according to claim 2, wherein $Ar_1$ represents a phenyl substituted with one or more substitutents selected from the group consisting of methyl, methoxy, amine, nitro, nitrile, or halogen selected from the group consisting of Cl, Br, and F.

20. A compound according to claim 3, wherein $Ar_1$ represents a phenyl substituted with one or more substitutents selected from the group consisting of methyl, methoxy, amine, nitro, nitrile, or halogen selected from the group consisting of Cl, Br, and F.

21. A compound according to claim 2, wherein $Ar_1$ represents a pyridyl radical.

22. A compound according to claim 3, wherein $Ar_1$ represents a pyridyl radical.

23. A compound according to claim 2, wherein $Ar_1$ represents a naphthyl.

24. A compound according to claim 3, wherein $Ar_1$ represents a naphthyl.

25. A compound according to claim 2, wherein X represents an oxygen atom.

26. A compound according to claim 3, wherein X represents an oxygen atom.

27. A compound according to claim 2, wherein X represents NH.

28. A compound according to claim 3, wherein X represents NH.

29. A compound according to claim 2, wherein X represents —$CH_2$—O.

30. A compound according to claim 3, wherein X represents —$CH_2$—O.

31. A compound according to claim 2, wherein X represents —$CH_2$—NH.

32. A compound according to claim 3, wherein X represents —$CH_2$—NH.

33. A method of treating a living animal in need thereof with an effective amount of a compound of claim 1 for the curative or preventive treatment of pain, depression, an obsessive compulsive disorders, an anxiety or panic attack, or cancer.

34. A method of claim 33 wherein the compound is selected from the group consisting of N-[4-methoxy-3-(4-methylpiperazin-1-yl)phenyl]-4-(2,3-dimethylphenyl) piperazin-1-ylamide and physiologically-acceptable acid addition salts thereof.

35. A pharmaceutical composition comprising an effective amount of a compound of claim 1 in combination with a pharmaceutically-acceptable vehicle.

36. A pharmaceutical composition of claim 35 wherein the compound is selected from the group consisting of N-[4-methoxy-3-(4-methylpiperazin-1-yl)phenyl]-4-(2,3-dimethylphenyl)piperazin-1-ylamide and physiologically-acceptable acid addition salts thereof.

37. Process for the preparation of a compound of formula (I) according to claim 1, in which $Ar_1$, $Ar_2$, and $R_1$ are defined as in claim 1 and X represents O or NH, characterized in that an intermediate of formula (III),

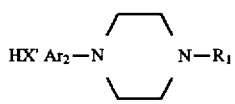
(III)

in which X' represents O or NH, and $Ar_2$ and $R_1$ are defined as in claim 1, and an arylpiperazine of formula (IV) in which $Ar_1$ is defined as in claim 1 is condensed with an electrophile of formula (XII)

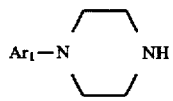
(IV)

(XII)

in which $X_1$ and $X_2$ represent a leaving group selected from the group consisting of halogen, an O-alkyl group, a succinimyl, a phthalyl, or imidazoyl.

38. A process of claim 37 wherein $X_1$ and $X_2$ are chlorine or an $OCCl_3$ group.

* * * * *

UNITED STATES PATENT AND TRADEMARK OFFICE
CERTIFICATE OF CORRECTION

PATENT NO. : 5,789,412
DATED : Aug. 4, 1998
INVENTOR(S) : S. Halazy, C. Jorand, P. Pauwels Page 1 of 4

It is certified that error appears in the above-indentified patent and that said Letters Patent is hereby corrected as shown below:

Title Page, OTHER PUBLICATIONS: "Buzzl et al, Chephalagia 15," should read: -- Buzzi et al., Cephalalgia 15 --.

[57] ABSTRACT, lines 6 and 7: Delete the following: "solvates, and physiologically-acceptable bioprecursors for their therapeutic use".

Column 1, line 32: "Huntington'" should read -- Huntington's --. Page 1, line 29

Column 4, line 33: Change "toxylate [sic]," to: -- tosylate --.
page 6, line 34

Column 9, line 21: "6.57 (8,3H);" should read: -- 6.57 (s,3H); --.

Column 14, line 52: "(9019/1) of" should read: -- (90/9/1) of --.

Column 15, line 23: At the end of the line, "$O_1H_2O$" should read -- $O_4.1H_2O$ --.

Column 15, line 27: "2.30 (8,3H);" should read: -- 2.30 (s,3H); --.

Column 16, line 21: In this line, "2316," should read -- 2816, --.

UNITED STATES PATENT AND TRADEMARK OFFICE
CERTIFICATE OF CORRECTION

PATENT NO. : 5,789,412
DATED : Aug. 4, 1998
INVENTOR(S) : S. Halazy, C. Jorand, P. Pauwels It is certified that error appears in the above-indentified patent and that said Letters Patent is hereby corrected as shown below:

Column 17, lines 41-42:  Delete "Com-" at the end of the line and begin a new paragraph with "Compound"....

Column 17, line 52:  "2.23 (8,3H);" should read -- 2.23 (s,3H); --.

Column 17, line 67:  "6.69 (d,1E);" should read: -- 6.69 (d,1H); --.

Column 18, line 65:  "2.33(8,3H);" should read -- 2.33 (s,3H); --.

Column 22, line 66:  "2.98 (m,4E);" should read -- 2.98 (m,4H); --.

Column 22, line 67:  "7.89 (d,1H1)." should read -- 7.89 (d,1H). --.

Column 26, line 14:  At the beginning of the line, "12H" should read -- 1H --.

Column 26, line 16:  "6.9-7.10 (m,5H);" should read -- 6.91-7.10 (m,5H); --.

UNITED STATES PATENT AND TRADEMARK OFFICE
CERTIFICATE OF CORRECTION

PATENT NO. : 5,789,412
DATED : Aug. 4, 1998
INVENTOR(S) : S. Halazy, C. Jorand, P. Pauwels Page 3 of 4

It is certified that error appears in the above-indentified patent and that said Letters Patent is hereby corrected as shown below:

Column 27, line 66: "2.23(8,3H);" should read
-- 2.23 (s,3H); --.

Column 29, line 40: "2.36 (8,3H);" should read
-- 2.36 (s,3H); --.

Column 35, line 20: At the end of the line,
"naphthalon-1-ol" should read -- naphthalen-1-ol --.
Page 55, line 29

Column 39, line 29: "N, 32.36;" should read
-- N, 12.36; --.

Column 42, line 46: "7.55 (c,8.0 Hz," should read
-- 7.55 (d,8.0 Hz, --.

Column 46, line 26: "Compound 53A" should read
-- Compound 51A --.

Column 46, line 61: "2.33(8,3H);" should read
-- 2.33 (s,3H); --.

Column 49, line 28: "3.84 (5.3H);" should read
-- 3.84 (s,3H); --.

UNITED STATES PATENT AND TRADEMARK OFFICE
CERTIFICATE OF CORRECTION

PATENT NO. : 5,789,412
DATED : Aug. 4, 1998
INVENTOR(S) : S. Halazy, C. Jorand, P. Pauwels It is certified that error appears in the above-indentified patent and that said Letters Patent is hereby corrected as shown below:

Column 54, line 49: Delete the word "and".

Column 56, line 47: "disorders," should read -- disorder, --.

Signed and Sealed this

Twenty-third Day of March, 1999

Attest:

Q. TODD DICKINSON

Attesting Officer

Acting Commissioner of Patents and Trademarks